(12) United States Patent
De Kock et al.

(10) Patent No.: US 11,077,297 B2
(45) Date of Patent: *Aug. 3, 2021

(54) ACTIVE MEDICAL DEVICE WITH ATTACHMENT FEATURES

(71) Applicant: CARDIAC PACEMAKERS, INC., St. Paul, MN (US)

(72) Inventors: Andrew L. De Kock, Ham Lake, MN (US); G. Shantanu Reddy, Minneapolis, MN (US); Lili Liu, Maple Grove, MN (US); James K. Cawthra, Jr., Ramsey, MN (US); Christopher Alan Fuhs, Roseville, MN (US); Peter Hall, Andover, MN (US); James O. Gilkerson, Stillwater, MN (US); Benjamin Philip Gundale, Plymouth, MN (US); Daniel J. Foster, Lino Lakes, MN (US); Henry J. Pepin, Loretto, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 468 days.

This patent is subject to a terminal disclaimer.

(21) Appl. No.: 15/955,331

(22) Filed: Apr. 17, 2018

(65) Prior Publication Data

US 2018/0296824 A1 Oct. 18, 2018

Related U.S. Application Data

(60) Provisional application No. 62/486,635, filed on Apr. 18, 2017.

(51) Int. Cl.
*A61N 1/05* (2006.01)
*A61M 25/09* (2006.01)
(Continued)

(52) U.S. Cl.
CPC .............. *A61N 1/05* (2013.01); *A61B 6/12* (2013.01); *A61B 8/0841* (2013.01); *A61M 25/09* (2013.01);
(Continued)

(58) Field of Classification Search
CPC ........ A61B 6/12; A61B 8/0841; A61M 25/09; A61N 1/05; A61N 1/0563; A61N 1/059; A61N 1/37518; A61N 1/39
See application file for complete search history.

(56) References Cited

U.S. PATENT DOCUMENTS

| | | |
|---|---|---|
| 5,331,966 A | 7/1994 | Bennett et al. |
| 6,647,292 B1 | 11/2003 | Bardy et al. |

(Continued)

FOREIGN PATENT DOCUMENTS

| | | |
|---|---|---|
| EP | 2818202 A1 | 12/2014 |
| EP | 3064131 A1 | 9/2016 |

(Continued)

OTHER PUBLICATIONS

Moeinipour et al., "A Rare Central Venous Catheter Malposition: A Case Report," Anesth Pain Med., 4(1): 1-3, Feb. 5, 2014.

(Continued)

*Primary Examiner* — Jocelin C Tanner
(74) *Attorney, Agent, or Firm* — Seager, Tufte & Wickhem LLP

(57) ABSTRACT

Implantable leads of a cardiac stimulus system are disclosed, as well as methods for implanting leads of a cardiac stimulus system. The lead may be comprised of a proximal portion having a coupler for coupling to an implantable pulse generator, an intermediate portion comprising a plurality of electrodes disposed thereon, and a distal portion. The intermediate portion may have a first diameter and the distal portion may have a second diameter. The distal portion may
(Continued)

also have an attachment feature for attaching to a lead pulling tool for delivery to an ITV and an intercostal vein. Methods may include pulling a lead from a first position to a second position within the vasculature, exiting the vasculature at the second location, and attaching a portion of the lead that exits the vasculature to an electrode or implantable device for use with the lead.

10 Claims, 39 Drawing Sheets

(51) Int. Cl.
- A61B 6/12 (2006.01)
- A61B 8/08 (2006.01)
- A61N 1/375 (2006.01)
- A61N 1/39 (2006.01)

(52) U.S. Cl.
CPC .......... *A61N 1/059* (2013.01); *A61N 1/0563* (2013.01); *A61N 1/37518* (2017.08); *A61N 1/39* (2013.01); *A61M 2025/09166* (2013.01)

(56) References Cited

U.S. PATENT DOCUMENTS

| | | | |
|---|---|---|---|
| 6,721,597 B1 | 4/2004 | Bardy et al. | |
| 7,149,575 B2 | 12/2006 | Ostroff et al. | |
| 7,287,995 B2 * | 10/2007 | Stein .................... | A61N 1/056 439/218 |
| 7,655,014 B2 | 2/2010 | Ko et al. | |
| 7,783,340 B2 | 8/2010 | Sanghera et al. | |
| 7,818,068 B2 | 10/2010 | Meadows et al. | |
| 7,962,222 B2 | 6/2011 | He et al. | |
| 8,005,543 B2 | 8/2011 | Libbus et al. | |
| 8,157,813 B2 | 4/2012 | Ko et al. | |
| 8,386,048 B2 | 2/2013 | McClure et al. | |
| 8,433,412 B1 | 4/2013 | Westlund et al. | |
| 8,483,843 B2 | 7/2013 | Sanghera et al. | |
| 8,543,216 B2 | 9/2013 | Carbunaru et al. | |
| 2005/0043765 A1 | 2/2005 | Williams et al. | |
| 2011/0022057 A1 * | 1/2011 | Eigler .................. | A61M 25/09 606/129 |
| 2012/0029335 A1 * | 2/2012 | Sudam .................... | A61N 1/05 600/374 |
| 2014/0114371 A1 | 4/2014 | Westlund et al. | |
| 2014/0330326 A1 | 11/2014 | Thompson-Nauman et al. | |
| 2015/0025612 A1 | 2/2015 | Haasl et al. | |
| 2015/0051610 A1 | 2/2015 | Schmidt et al. | |
| 2015/0196756 A1 | 7/2015 | Stahmann et al. | |
| 2015/0196757 A1 | 7/2015 | Stahmann et al. | |
| 2015/0196758 A1 | 7/2015 | Stahmann et al. | |
| 2015/0196769 A1 | 7/2015 | Stahmann et al. | |
| 2015/0224320 A1 | 8/2015 | Stahmann | |
| 2015/0297902 A1 | 10/2015 | Stahmann et al. | |
| 2015/0360036 A1 | 12/2015 | Kane et al. | |
| 2016/0038742 A1 | 2/2016 | Stahmann et al. | |
| 2016/0059007 A1 | 3/2016 | Koop | |
| 2016/0059022 A1 | 3/2016 | Stahmann et al. | |
| 2016/0059024 A1 | 3/2016 | Stahmann et al. | |
| 2016/0059025 A1 | 3/2016 | Stahmann et al. | |
| 2016/0067478 A1 | 3/2016 | McGeehan et al. | |
| 2016/0089539 A1 | 3/2016 | Gilkerson et al. | |
| 2016/0228712 A1 | 8/2016 | Koop | |
| 2016/0256692 A1 | 9/2016 | Baru | |
| 2017/0021159 A1 | 1/2017 | Reddy et al. | |
| 2017/0112399 A1 | 4/2017 | Brisben et al. | |
| 2017/0113040 A1 | 4/2017 | Brisben et al. | |
| 2017/0113050 A1 | 4/2017 | Brisben et al. | |
| 2017/0113053 A1 | 4/2017 | Brisben et al. | |
| 2018/0036527 A1 | 2/2018 | Reddy et al. | |
| 2018/0036547 A1 | 2/2018 | Reddy | |
| 2018/0133462 A1 | 5/2018 | Reddy | |
| 2018/0133463 A1 | 5/2018 | Reddy | |
| 2018/0133494 A1 | 5/2018 | Reddy | |
| 2018/0169384 A1 | 6/2018 | Reddy et al. | |
| 2018/0169425 A1 | 6/2018 | Reddy et al. | |
| 2018/0178018 A1 | 6/2018 | Reddy et al. | |
| 2018/0178019 A1 | 6/2018 | Reddy et al. | |
| 2018/0193060 A1 | 7/2018 | Reddy et al. | |
| 2018/0214686 A1 | 8/2018 | De Kock et al. | |
| 2018/0256890 A1 * | 9/2018 | Fuhs .................... | A61N 1/056 |
| 2018/0264270 A1 | 9/2018 | Koop et al. | |
| 2018/0296824 A1 | 10/2018 | De Krock et al. | |
| 2018/0325480 A1 | 11/2018 | Liu et al. | |
| 2018/0344200 A1 | 11/2018 | Thakur et al. | |
| 2018/0344252 A1 | 11/2018 | An et al. | |

FOREIGN PATENT DOCUMENTS

| | | |
|---|---|---|
| WO | 2016148928 A1 | 9/2016 |
| WO | 2016149262 A1 | 9/2016 |

OTHER PUBLICATIONS

Schuder et al., "Experimental Ventricular Defibrillation with an Automatic and Completely Implanted System," Trans. Amer. Soc. Artif. Int. Organs, XVI: 207-212, 1970.

Schuder et al., "The Role of an Engineering Oriented Medical Research Group in Developing Improved Methods and Devices for Achieving Ventricular Defibrillation: The University of Missouri Experience," PACE, 16: 95-124, Jan. 1993.

Ghosh et al., "A Rare Malposition of the Thoracic Venous Catheter Introduced via the Left Internal Jugular Vein," Indian J. Crit. Care Med., 12(4): 201-203, Oct.-Dec. 2008.

Loukas et al., "The Clinical Anatomy of the Internal Thoracic Veins," Folia Morphol, 66(1): 25-32, 2007.

Kondo et al., "Successful Intermuscular Implantation of Subcutaneous Implantable Cardioverter Difibrillator in a Japanese Patient with Pectus Exacavatum," Journal of Arrhythmia, 33(1): 63-65, 2016.

International Search Report and Written Opinion dated Jun. 26, 2018 for International Application No. PCT/US2018/027965.

Advisory Action Before the Filing of an Appeal Brief for U.S. Appl. No. 15/667,167, dated Mar. 21, 2019.

Final Office Action for U.S. Appl. No. 15/667,167, dated Jan. 10, 2019.

Non-Final Office Action for U.S. Appl. No. 15/667,167, dated Jun. 26, 2018.

Non-Final Office Action for U.S. Appl. No. 15/667,167, dated Aug. 7, 2019.

Final Office Action for U.S. Appl. No. 15/667,221, dated Apr. 11, 2019.

Non-Final Office Action for U.S. Appl. No. 15/667,221, dated Oct. 1, 2018.

Notice of Allowance and Fees Due for U.S. Appl. No. 15/667,221, dated Jul. 11, 2019.

Amendment for U.S. Appl. No. 15/667,167, dated Sep. 17, 2018.
Amendment for U.S. Appl. No. 15/667,167, dated Oct. 9, 2019.
Amendment After Final Office Action for U.S. Appl. No. 15/667,167, dated Mar. 11, 2019.

Request for Continued Examination (RCE) for U.S. Appl. No. 15/667,167, dated Apr. 10, 2019.

Amendment for U.S. Appl. No. 15/667,221, dated Dec. 21, 2018.
Amendment After Final Office Action for U.S. Appl. No. 15/667,221, dated May 22, 2019.

* cited by examiner

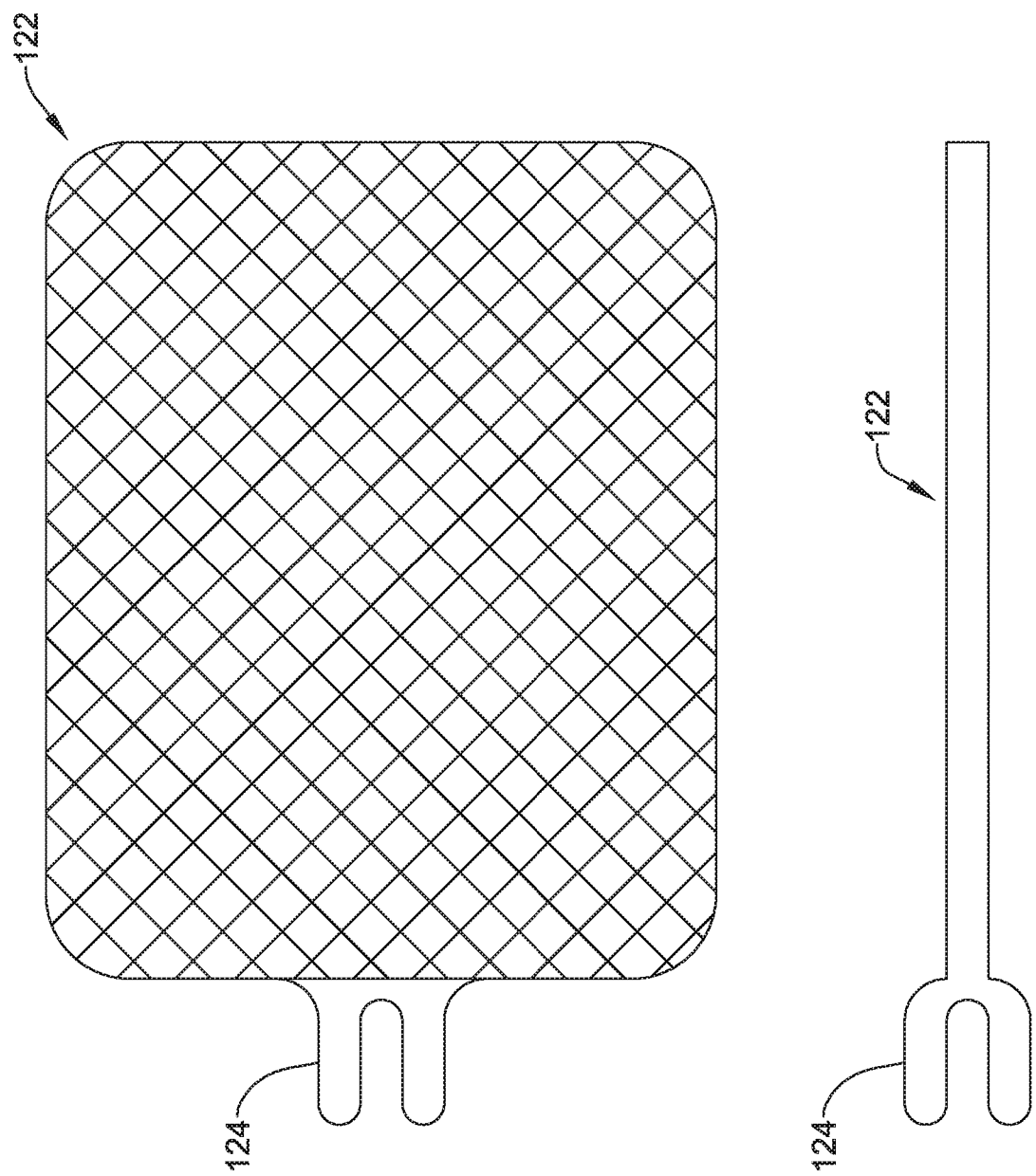

ACTIVE MEDICAL DEVICE WITH ATTACHMENT FEATURES

CROSS REFERENCE TO RELATED APPLICATIONS

The present application claims the benefit of and priority to U.S. Provisional Patent Application Ser. No. 62/486,635, filed Apr. 18, 2017, titled ACTIVE MEDICAL DEVICE WITH ATTACHMENT FEATURES, the disclosure of which is incorporated herein by reference.

BACKGROUND

The implantable defibrillator has been demonstrated to extend patient lives by treatment of potentially deadly arrhythmias. Over time, various efforts have been made to address complications associated with implantation of such devices. For example, early devices generally used epicardial patch electrodes implanted via thoracotomy, with attendant surgical risks and significant risks of failure of the epicardial patch electrodes and associated leads. The use of transvenous leads represented a major advance, avoiding the thoracotomy and improving reliability. However, lead failure remained a significant issue, as the lead attachment in the heart caused the lead to flex with each heartbeat. The advent of subcutaneous defibrillators allows avoidance of these lead failure issues, with leads implanted beneath the skin and over the ribcage of the patient and not subjected to repeated flexing.

However, subcutaneous defibrillators require higher energy for defibrillation, causing the pulse generators for such systems to be larger than their transvenous predecessors, and both bradycardia pacing and anti-tachycardia pacing are of limited utility as such pacing subcutaneously can be very uncomfortable for the patient. This has led to interest in further alternative locations for implantable defibrillators, pacemakers and cardiac resynchronization therapy devices. With such interest there is a need for new and alternative delivery methods and designs of implantable defibrillators, implantable pacemakers, and other medical devices.

Overview

The present inventors have recognized, among other things, that the internal thoracic vasculature including, in particular, the internal thoracic vein (ITV), sometimes also referred to as the internal mammary vein, presents an opportunity for an additional alternative implant location. For such illustrative uses, and other uses, an IMD having a lead may be comprised of a proximal portion having a coupler for coupling to an implantable pulse generator, an intermediate portion comprising a plurality of electrodes disposed thereon, and a distal portion. The intermediate portion may have a first diameter and the distal portion may have a second diameter. The distal portion may also have an attachment feature for attaching to a lead pulling tool for delivery to an ITV and an intercostal vein. Illustrative methods for using or implanting such a system may include pulling a lead from a first position to a second position within the vasculature, exiting the vasculature at the second location, and attaching a portion of the lead that exits the vasculature to an electrode for use with the lead.

A first non-limiting example takes the form of an implantable lead for use with a cardiac stimulation device, the lead comprising a proximal portion having a coupler for coupling to an implantable pulse generator, an intermediate portion comprising a plurality of electrodes disposed thereon, and a distal portion, wherein the intermediate portion has a first outer diameter and the distal portion has a second outer diameter, the second outer diameter being less than the first outer diameter, further wherein the distal portion of the lead has a portion of at least four centimeters length with an outer diameter of no greater than 2 French.

Additionally or alternatively a second non-limiting example take the form of a lead as in the first non-limiting example wherein the distal portion of the lead comprises an attachment feature adapted for attachment to a lead pulling tool for emplacing the lead in the vasculature of a patient.

Additionally or alternatively a third non-limiting example takes the form of a lead as in the first to second non-limiting examples wherein the distal portion of the lead includes only a single electrical conductor therein, further wherein the distal portion of the lead comprises a first part in which the single electrical conductor is insulated and a second part in which the single electrical conductor is not insulated, further wherein the intermediate portion comprises multiple conductors to electrically link at least first and second electrodes of the intermediate portion to the coupler.

Additionally or alternatively a fourth non-limiting example takes the form of a lead as in the first to third non-limiting examples wherein the distal portion of the lead is adapted for placement in an intercostal vein, and the intermediate portion is adapted for placement in an internal thoracic vein.

A fifth non-limiting example takes the form of a lead kit comprising a lead as in the first to fourth non-limiting examples and an electrode for coupling to the lead after the lead has been at least partly implanted in a blood vessel of a patient, wherein the distal portion of the lead comprises an attachment feature adapted for attachment to the electrode, and the electrode comprises a connector to mate with the attachment feature of the lead.

A sixth non-limiting example takes the form of an implantable kit comprising a lead as in the first to fourth non-limiting examples or a lead kit as in the fifth non-limiting example further comprising a lead pulling tool having a distal end adapted for passing through an internal thoracic vein of a patient and a proximal end having an attachment structure for coupling to the distal portion of the lead.

A seventh non-limiting example takes the form of an implantable lead for use with a cardiac stimulation device, the lead comprising a proximal end having a first coupler for coupling to an implantable pulse generator, an intermediate portion comprising a plurality of electrodes disposed thereon, and a distal portion of the lead having an attachment feature, wherein the intermediate portion has a first outer diameter and the distal portion has a second outer diameter, the second outer diameter being less than the first outer diameter.

Additionally or alternatively an eighth non-limiting example takes the form of a lead as in the seventh non-limiting example wherein the attachment feature includes a threaded portion.

Additionally or alternatively a ninth non-limiting example takes the form of a lead as in the eighth non-limiting example wherein the threaded portion is a female thread.

Additionally or alternatively a tenth non-limiting example takes the form of a lead as in the eighth non-limiting example wherein the threaded portion is a male thread.

Additionally or alternatively an eleventh non-limiting example takes the form of a lead as in the seventh to tenth non-limiting examples wherein the attachment feature includes a hole configured to match with a fastener.

Additionally or alternatively a twelfth non-limiting example takes the form of a lead as in the seventh to eleventh non-limiting examples wherein the attachment feature includes a first ridge portion configured to match with a second ridge portion.

Additionally or alternatively a thirteenth non-limiting example takes the form of a lead as in the seventh to twelfth non-limiting examples wherein the distal portion of the lead has a portion of at least four centimeters length with an outer diameter of no greater than 2 French.

A fourteenth non-limiting example takes the form of a lead kit comprising a lead as in the seventh to thirteenth non-limiting examples and a shock electrode for coupling to the attachment feature after the lead has been at least partly implanted in a blood vessel of a patient.

A fifteenth non-limiting example takes the form of an implantable kit comprising a lead as in the seventh to thirteenth non-limiting examples or a lead kit as in the fourteenth non-limiting examples and further comprising a lead pulling tool with a proximal end and a distal end, the distal end adapted to traverse the ITV and/or intercostal vein, the proximal end having a proximal tip portion to attach to the attachment feature of the lead for pulling the lead into position.

A sixteenth non-limiting example takes the form of an implantable lead for use with a cardiac stimulation device, the lead comprising a proximal end having a coupler for coupling to an implantable pulse generator, an intermediate portion comprising a plurality of electrodes disposed thereon, and a distal portion of the lead, wherein the intermediate portion has a first outer diameter and the distal portion has a second outer diameter, the second outer diameter being less than the first outer diameter, further wherein the distal portion of the lead has a portion of at least four centimeters length with an outer diameter of no greater than 2 French.

Additionally or alternatively a seventeenth non-limiting example takes the form of a lead as in the sixteenth non-limiting example wherein the distal portion of the lead comprises an attachment feature adapted for attachment to a lead pulling tool for emplacing the lead in the vasculature of a patient.

Additionally or alternatively an eighteenth non-limiting example takes the form of a lead as in the sixteenth non-limiting example wherein the distal portion of the lead includes only a single electrical conductor therein, further wherein the distal portion of the lead comprises a first part in which the single electrical conductor is insulated and a second part in which the single electrical conductor is not insulated, further wherein the intermediate portion comprises multiple conductors to electrically link at least first and second electrodes of the intermediate portion to the coupler.

Additionally or alternatively a nineteenth non-limiting example takes the form of a lead as in the sixteenth non-limiting example wherein the distal portion of the lead is adapted for placement in an intercostal vein, and the intermediate portion is adapted for placement in an internal thoracic vein.

A twentieth non-limiting example takes the form of a lead kit comprising a lead as in the sixteenth non-limiting example and an electrode for coupling to the lead after the lead has been at least partly implanted in a blood vessel of a patient, wherein the distal portion of the lead comprises an attachment feature adapted for attachment to the electrode, and the electrode comprises a connector to mate with the attachment feature of the lead.

A twenty-first non-limiting example takes the form of an implantation kit comprising a lead kit as in the twentieth non-limiting example and further comprising a lead pulling tool having a distal end adapted for passing through an internal thoracic vein of a patient and a proximal end having an attachment structure for coupling to the distal portion of the lead.

A twenty-second non-limiting example takes the form of an implantable lead for use with a cardiac stimulation device the lead comprising a proximal end having a first coupler for coupling to an implantable pulse generator, an intermediate portion comprising a plurality of electrodes disposed thereon, and a distal portion of the lead having an attachment feature, wherein the intermediate portion has a first outer diameter and the distal portion has a second outer diameter, the second outer diameter being less than the first outer diameter.

Additionally or alternatively a twenty-third non-limiting example takes the form of a lead as in the twenty-second non-limiting example wherein the attachment feature includes a threaded portion.

Additionally or alternatively a twenty-fourth non-limiting example takes the form of a lead as in the twenty-third non-limiting example wherein the threaded portion is a female thread.

Additionally or alternatively a twenty-fifth non-limiting example takes the form of a lead as in the twenty-third non-limiting example wherein the threaded portion is a male thread.

Additionally or alternatively a twenty-sixth non-limiting example takes the form of a lead as in the twenty-second non-limiting example wherein the attachment feature includes a hole configured to match with a fastener.

Additionally or alternatively a twenty-seventh non-limiting example takes the form of a lead as in the twenty-second non-limiting example wherein the attachment feature includes a first ridge portion configured to match with a second ridge portion.

Additionally or alternatively a twenty-eighth non-limiting example takes the form of a lead as in the twenty-second non-limiting example wherein the distal portion of the lead has a portion of at least four centimeters length with an outer diameter of no greater than 2 French.

A twenty-ninth non-limiting example takes the form of a lead kit comprising a lead as in the twenty-second non-limiting example and a shock electrode for coupling to the attachment feature after the lead has been at least partly implanted in a blood vessel of a patient.

A thirtieth non-limiting example takes the form of an implantation kit comprising a lead as in the twenty-ninth non-limiting example further comprising a lead pulling tool with a proximal end and a distal end, the distal end adapted to traverse the ITV and/or intercostal vein, the proximal end having a proximal tip portion to attach to the attachment feature of the lead for pulling the lead into position.

A thirty-first non-limiting example takes the form of a method of implanting a lead for use in a cardiac stimulus system in a patient comprising establishing access to a brachiocephalic vein of the patient, advancing a distal end of a lead pulling tool from the brachiocephalic vein to and into an internal thoracic vein (ITV), obtaining a location of the lead pulling tool in the venous vasculature, establishing an external access to the lead pulling tool, attaching the attachment feature of the lead to a proximal tip portion located on a proximal end of the lead pulling tool, and drawing the lead into the ITV by pulling on the lead pulling tool using the external access. The location of the lead pulling tool may be, for example and a specified in additional examples, in the ITV or in an intercostal vein, or in a different blood vessel such as an azygos vein, hemiazygos vein, accessory hemiazygos vein, or the superior epigastric vein.

Additionally or alternatively a thirty-second non-limiting example takes the form of a method as in the thirty-first non-limiting example wherein the external access to the lead pulling tool is in the ITV.

Additionally or alternatively a thirty-third non-limiting example takes the form of a method as in the thirty-second non-limiting example further comprising detaching the attachment feature of the lead from the proximal tip portion of the lead pulling tool using the external access.

Additionally or alternatively a thirty-fourth non-limiting example takes the form of a method as in the thirty-third non-limiting example further comprising advancing at least the attachment feature of the lead subcutaneously in the patient, establishing a second external access to the attachment feature, and attaching the attachment feature of the lead to a connector included on an electrode using the second external access.

Additionally or alternatively a thirty-fifth non-limiting example takes the form of a method as in the thirty-second non-limiting example further comprising advancing a portion of the distal end of the lead pulling tool from the ITV to the intercostal vein, establishing access to the intercostal vein by placing a dilator and an introducer sheath over the portion of the distal end of the lead pulling tool, and advancing at least the attachment feature of the lead into the intercostal vein using the introducer sheath.

Additionally or alternatively a thirty-sixth non-limiting example takes the form of a method as in the thirty-fifth non-limiting example further comprising establishing a second external access to the attachment feature, and attaching the attachment feature of the lead to a connector included on an electrode using the second external access.

Additionally or alternatively a thirty-seventh non-limiting example takes the form of a method as in the thirty-first non-limiting example wherein the external access to the lead pulling tool is in an intercostal vein.

Additionally or alternatively a thirty-eighth non-limiting example takes the form of a method as in the thirty-seventh non-limiting example further comprising advancing a portion of the distal end of the lead pulling tool from the ITV to the intercostal vein, drawing at least the attachment feature of the lead into the intercostal vein by pulling on the lead pulling tool using the external access.

Additionally or alternatively a thirty-ninth non-limiting example takes the form of a method as in the thirty-eighth non-limiting example further comprising detaching the attachment feature of the lead from the proximal tip portion of the lead pulling tool using the external access.

Additionally or alternatively a fortieth non-limiting example takes the form of a method as in the thirty-ninth non-limiting example further comprising attaching the attachment feature of the lead to a connector included on an electrode using the external access.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 1B-1F illustrate exemplary shocking elements;

DETAILED DESCRIPTION

Figure 1A:
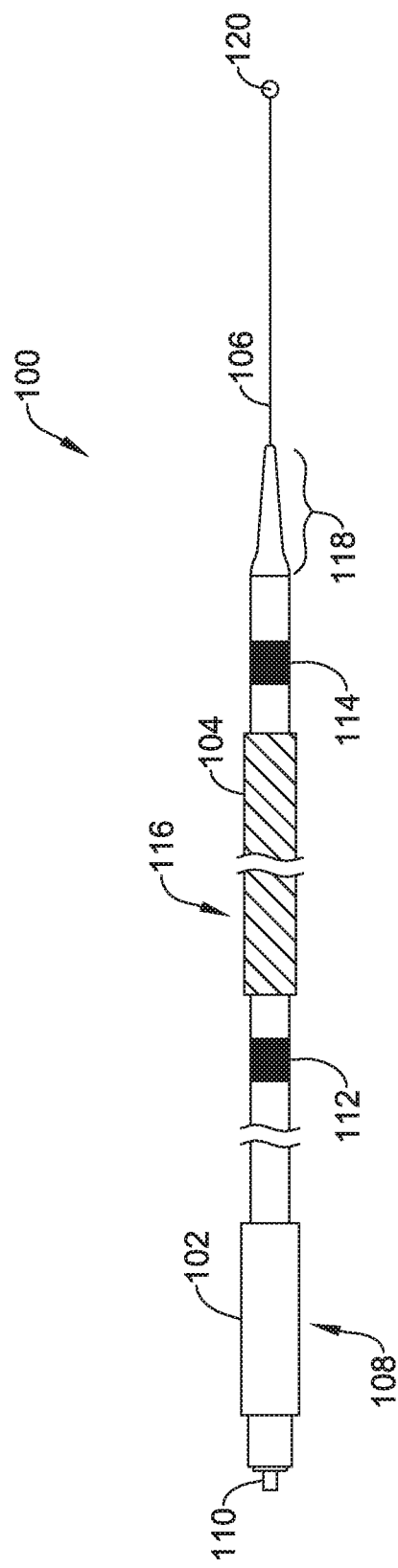
FIG. 1A illustrates an exemplary lead.

The S-ICD System from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

While many patients can be well treated with the S-ICD System, there continue to be limitations. Increased energy requirements of the S-ICD System, perceived difficulty with providing chronic bradycardia pacing, and unavailability of anti-tachycardia pacing to terminate select fast tachycardias, have created interest in alternative defibrillator and/or pacemaker placement techniques. One proposal has included a substernal placement, with a lead extending beneath the sternum from a position inferior to the lower rib margin, such as in U.S. patent application Ser. No. 15/208,682, titled SUBSTERNAL PLACEMENT OF A PACING OR DEFIBRILLATING ELECTRODE, the disclosure of which is incorporated herein by reference. Proposals for a substernal device have been referred to as extravascular, insofar as the lead does not enter or reside in the vasculature. Such devices are distinct from early generation epicardial devices in that the lead and electrode would not touch the heart or enter or be secured to the pericardium.

The internal thoracic vein (ITV), which may also be referred to as the internal mammary vein, is a vessel that drains the chest wall and breasts. There are both left and right internal thoracic veins on either side of the sternum, beneath the ribs. The ITV arises from the superior epigastric vein, accompanies the internal thoracic artery along its course and terminates in the brachiocephalic vein. Use of this vessel for cardiac device implantation is discussed in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference. The inventors have recognized that the ITV may make a suitable location for placement of a cardiac stimulus lead, such as the leads discussed in U.S. patent application Ser. No. 15/846,060, titled LEAD WITH INTEGRATED ELECTRODES, the disclosure of which is incorporated herein by reference and U.S. patent application Ser. No. 15/846,081, titled IMPLANTATION OF AN ACTIVE MEDICAL DEVICE USING THE INTERCOSTAL VEIN, the disclosure of which is incorporated herein by reference. While much of the following disclosure focuses on the use of the ITV, many of these concepts could also be applied to the internal thoracic arteries, which may sometimes be referenced as the internal mammary arteries.

FIG. 1A illustrates an example of a shock coil lead 100 configured for emplacement in the vasculature of a patient using methods of delivery described herein. The lead 100 may be manufactured of any suitable material and by any suitable manner. For example, numerous polymers are known for lead manufacture. Internal longitudinal or lateral support members, such as braids, core wires, etc. may be provided. Extrusion or molding may be used. Internal conductors may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The leads may include on all or a portion thereof various coatings such as an anti-microbial coating to reduce the likelihood, severity, and/or progression of infection.

In various embodiments, the lead 100 may have a proximal portion 102, an intermediate portion 104, and a distal portion 106. In some cases, the proximal portion 102 may include a terminal 108 having a coupler 110 for coupling the lead 100 to an implantable pulse generator (not shown in FIG. 1A). Moreover, the terminal 108 may be capable of high voltage transmission to and from the coupler 110. In certain embodiments, the intermediate portion 104 may include two sensing/pacing electrodes 112 and 114 and at least one coil electrode 116. In various embodiments, the intermediate portion 104 may also include multiple conductors configured to electrically link the two sensing/pacing electrodes 112 and 114 and/or the coil electrode 116 to the terminal 108. In some examples, the coil electrode 116 and the sensing/pacing electrodes 112 and 114 may be electrically isolated from each other by simple spacing, or by using any of the methods and structures discussed in U.S. patent application Ser. No. 15/846,060, titled LEAD WITH INTEGRATED ELECTRODES, the disclosure of which is incorporated herein by reference. In another example, the coil electrode 116 is a single electrode extending between and under the sensing/pacing electrodes 112 and 114.

As shown, the intermediate portion 104 may also have a tapered distal end 118. As a result, the lead body 100 may transition from a first (larger) outer diameter of the intermediate portion 104 to a second (smaller) outer diameter of the distal portion 106. In some embodiments, the smaller outer diameter of the distal portion 106 may allow the distal portion 106 to be implanted in an intercostal vein of the patient while the intermediate portion 104 may be implanted in an ITV of the patient.

In some cases, the distal portion 106 may include a single electrical conductor, and may have an outer diameter between 0.5 French and 2 French, and a length of at least four centimeters. In certain embodiments, parts of the electrical conductor may be insulated and other parts of the electrical conductor may not be insulated. In an example, the distal portion may take the form of a microcatheter or microcable configuration as those terms are used in the art. For example, a lead with a microcable or microcatheter distal configuration may have a distal portion with an outer diameter in the range of up to 3 French.

According to various embodiments, a distal tip 120 of the distal portion 106 may include an attachment feature for attaching the lead 100 to an attachable/detachable shocking element. FIG. 1B shows a top-view and a side-view of an illustrative shocking element. In this embodiment, the shocking element is a mesh patch electrode 122. In accordance with the principles of the present invention, the mesh patch electrode 122 may have a tissue interface of the type conventionally known in the art and used for delivery of high energy defibrillating shock. Accordingly, the mesh patch electrode 122 may be planar (as can be seen from the side-view of FIG. 1B) and shaped to provide an essentially rectangular base region (as can be seen from the top-view of FIG. 1B). In some examples, the mesh patch electrode 122 may be flexible and the mesh may be composed of a conductive material such as titanium wire, carbon, metal carbide, metal nitride, and metal oxide. Furthermore, the patch may be completely surface-coated by the carbon and the metal compounds noted. The metals should be non-toxic and biocompatible. In some examples, the mesh patch electrode 122 may have motion sensors, such as piezoelectric sensors, integrated in the mesh. In certain embodiments, the mesh patch electrode 122 may be configured for placement in an axillary position of the patient. In another example, the mesh patch electrode 122 may be implanted in a subclavicular location, historically a common place to put an implanted canister for a transvenous defibrillator or pacemaker. However, other locations may be used for implantation of the mesh patch electrode 122.

In various embodiments, the mesh patch electrode 122 may include a connector 124 to mate with the attachment feature of the lead. The connector may be manufactured of any suitable material and by any suitable manner. For example, the connector may need to transmit electrical current from the lead 100 to the mesh patch electrode 122. Therefore, in certain embodiments, the connector may be composed of stainless steel, titanium, gold, silver, or any other conductive material may be used.

Figure 1C:
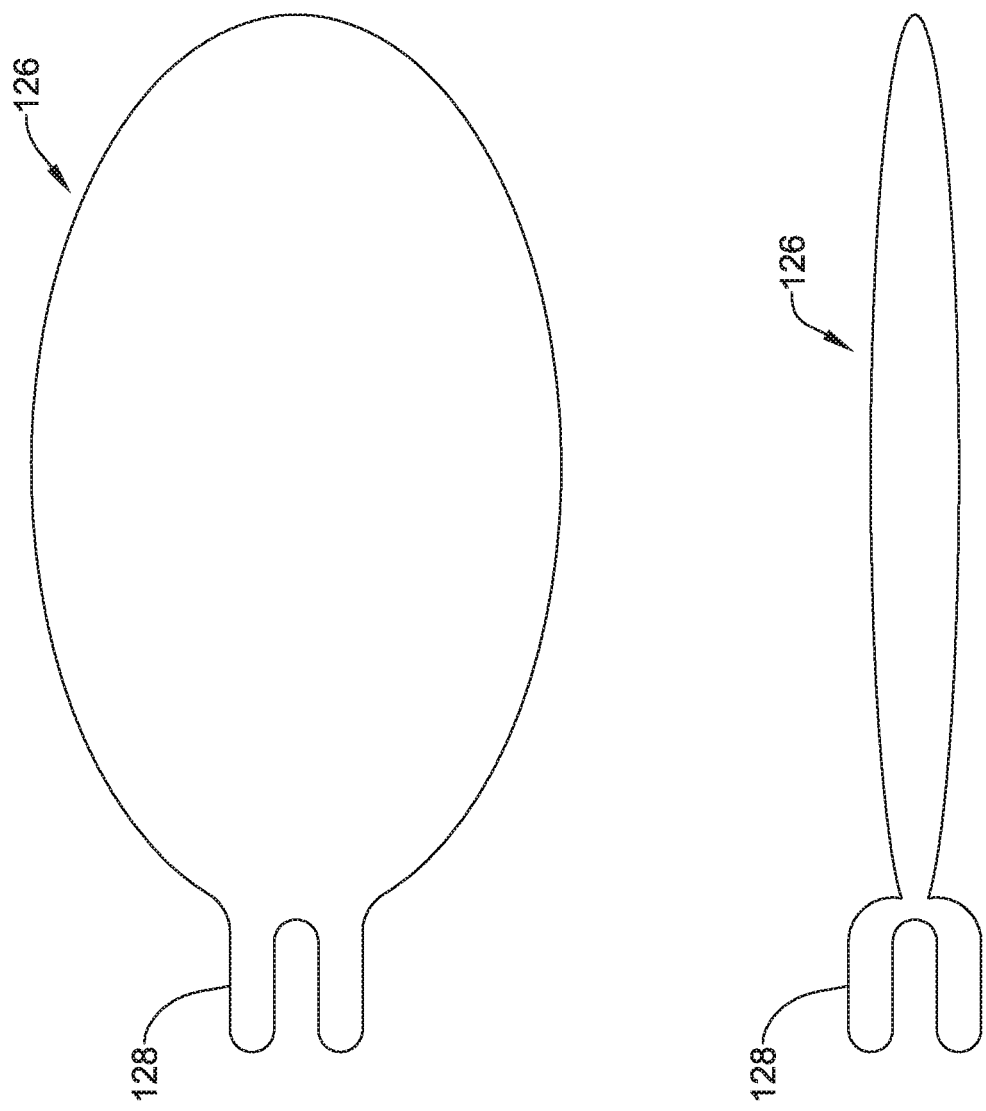

FIG. 1C shows a top-view and a side-view of another illustrative shocking element. In this embodiment, the shocking element is a solid disk electrode 126. The solid disk electrode 126 may be configured and operate similar to the mesh patch electrode and be implanted at similar locations within the patient. However, the exterior solid disk electrode 126 may have a smooth exterior. Moreover, the electrode disks may be round, oval, or square; however, other shapes may be employed without departing from the scope of the invention. For purposes of illustration, the solid disk electrode 126 is depicted as being oval in shape. In various embodiments, the solid disk electrode 126 may also include a connector 128 to mate with the attachment feature of the lead 100, similar to the connector 124.

Figure 1D:
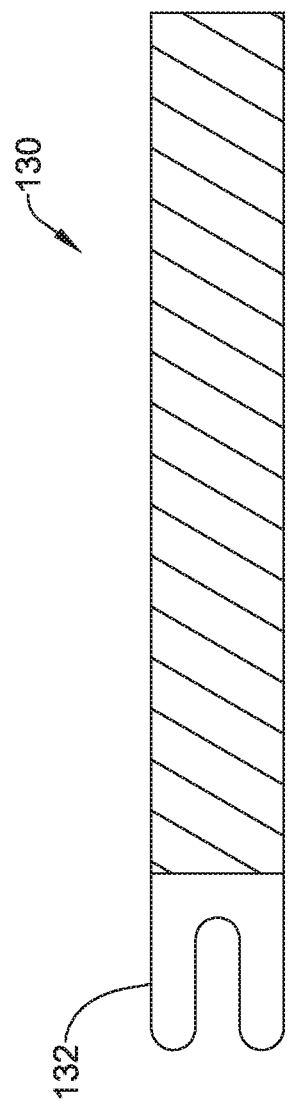

FIG. 1D shows another illustrative shocking element. In this embodiment, the shocking element is a coil electrode 130. The coil electrode 130 may operate similar to the electrodes 122 and 128 and be implanted at similar locations within the patient. In some examples, the coil electrode 130 may have insulated ring electrodes located along the length of the coil electrode 130. In some examples, the coil electrode 130 may be made up of coil segments that could be connected together as a group, or which may be separately addressable. If desired, each individual ring or coil segment may be utilized as a pacing cathode or anode or, in the alternative, as a sensing electrode. If a high voltage shock is desirable, the coil segments and/or ring electrodes may be activated to deliver a shock, or alternatively one or more segments or ring electrodes may be inactive (such as set in a high impedance state or allowed to float, electrically speaking) during high voltage therapy delivery. In various embodiments, the coil electrode 130 may also include a connector 132 to mate with the attachment feature of the lead 100, similar to the connector 124.

Figure 1E:
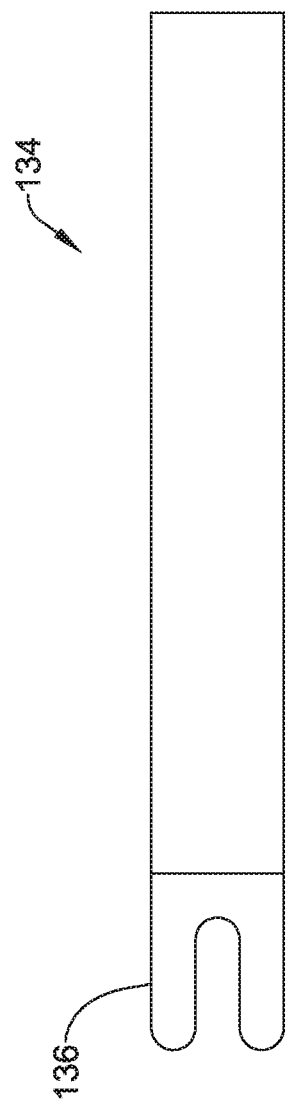

FIG. 1E shows another illustrative shocking element. In this embodiment, the shocking element is a rod electrode 134. The rod electrode 134 may be used for delivery of high energy defibrillating shock. Accordingly, the rod electrode 134 may be configured to operate similar to the electrodes 122, 128, and 134 described above and be implanted at similar locations within the patient. In addition, the rode electrode 134 may also include a connector 136 to mate with the attachment feature of the lead 100, similar to the connector 124.

Figure 1F:
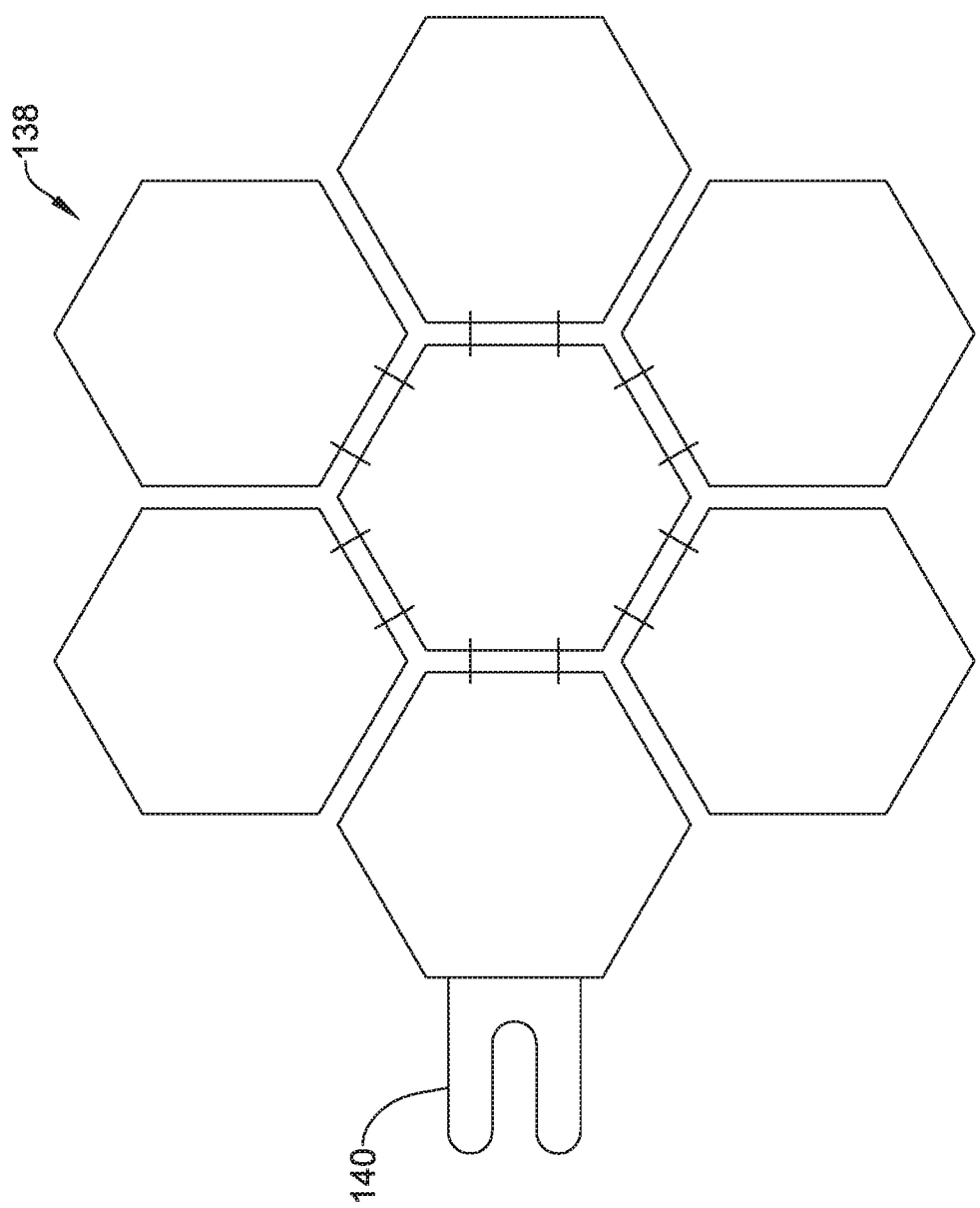

FIG. 1F shows another illustrative shocking element. In this embodiment, the shocking element is a jointed disk array 138. The jointed disk array 138 may be configured to operate similar to the sold disk electrode 126 and be implanted at similar locations within the patient. However, the jointed disk array 138 may be configured to contact a larger surface area of the patient. Accordingly, the jointed disk array 138 may provide flexibility on the larger surface area. The jointed disk array 138 may also be coated with e-spin or Gore membrane to prevent tissue ingrowth. The jointed disk array 138 may also contain multiple "rings" and take on a unique outer shape.

This list of shocking elements is by no means exhaustive. In some cases, the shocking elements may include other configurations that facilitate cardiac therapy. As such, the final design may be optimized for a multiple of factors including shock efficacy, reliability, patient comfort, and ease of use.

According to various embodiments, the attachment feature of the lead may also be used to attach the lead 100 to a lead pulling tool and emplacing the lead 100 in the vasculature of a patient. Certain embodiments of the attachment feature will now be described. These attachment features may be manufactured of any suitable material and by any suitable manner. For example, as stated above, the distal end 120, including the attachment feature, may be comprised of a single electrical conductor. Accordingly, the attachment feature may be formed of stainless steel, titanium, gold, silver, or any other conductive material may be used.

Figure 2A:
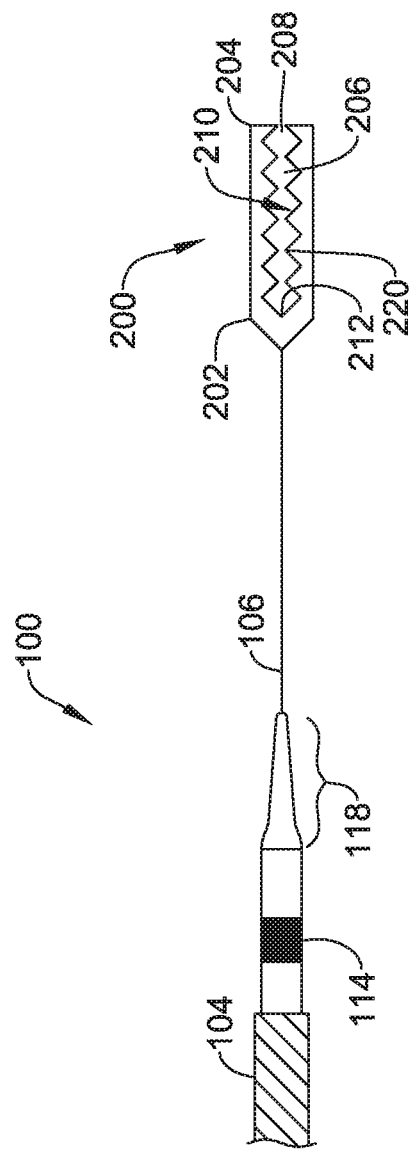
FIGS. 2A-2C illustrate the exemplary lead with an exemplary attachment feature.
Figure 2B:
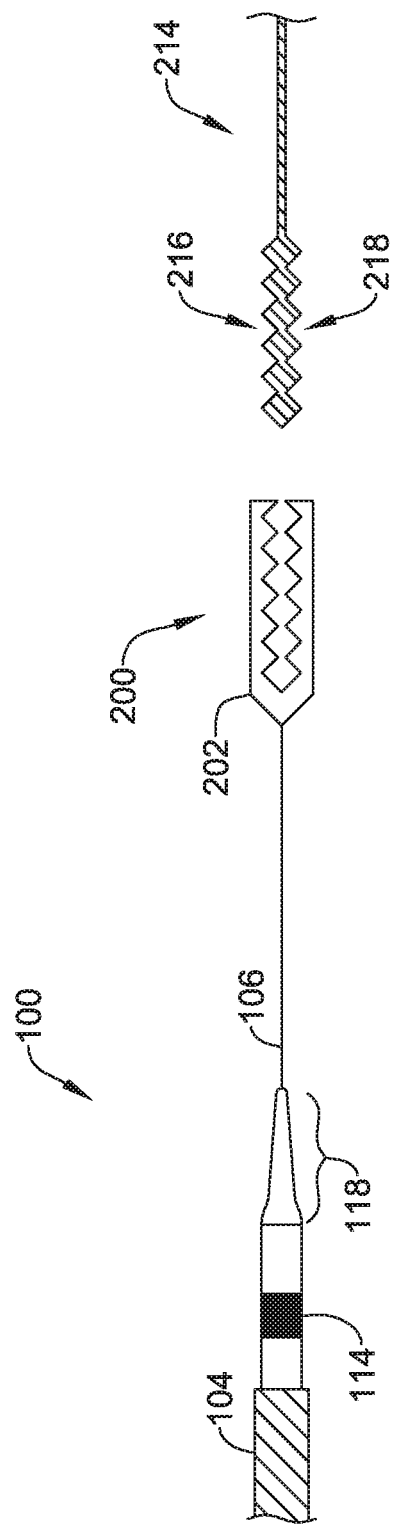
Figure 2C:
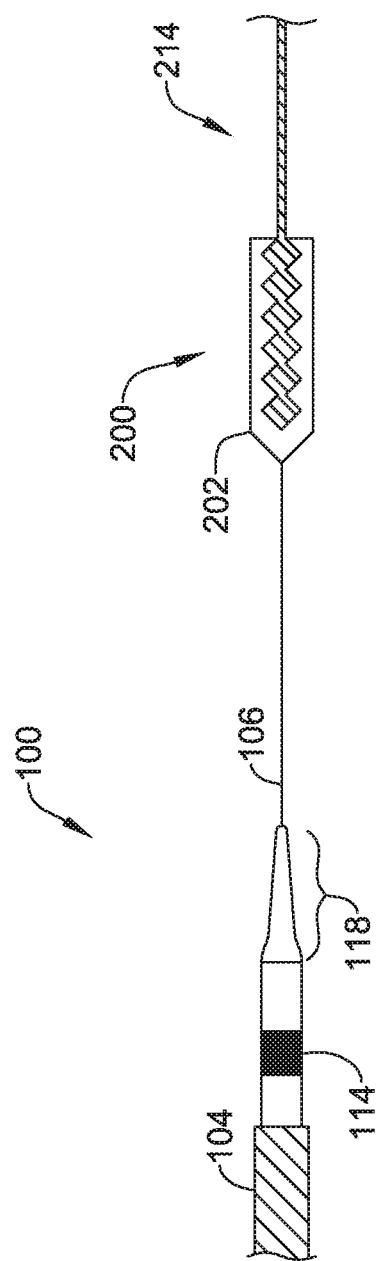

FIG. 2A-2C show the lead 100 with a cross-sectional view of an illustrative attachment feature. For clarity, the attachment feature has been enlarged in FIGS. 2A-2C. According to various embodiments, the attachment feature may have an outer diameter between 0.5 French and 2 French, similar to the distal portion 106. Referring to FIG. 2A-2C, the attachment feature may be a shell 200 having a first end 202 and an opposing second end 204. The first end 202 may be coupled to the distal end 120 of the lead 100 by any suitable means or, in other embodiments, the distal end 120 and the shell 200 may be one continuous, single, element. In various embodiments, the shell 200 may have an inner cavity 206. Moreover, an inner wall 210 of the cavity 206 may be comprised of threads 220 (e.g., "female threads") that extend from an edge 212 of the first end 202 over a sufficient axial distance of the inner wall 210. The second end 204 may also have an opening 208. Turning to FIG. 2B, the opening 208 may be configured to allow a proximal tip portion of a lead pulling tool 214 to enter the cavity 206. In some cases, the proximal tip portion may be an elongated member 216 having external threads 218 (e.g., "male threads") to interweave with the threads 220 of the shell 200. As shown in FIG. 2C, when the elongated member 216 moves from the opening 208 to the edge 212 of the first end 202, the elongated member 216 may become increasingly tightened to the shell 200. As a result, the lead pulling tool 214 may become coupled to the lead 100. In some examples, the coupling of the lead 100 to the lead pulling tool 214 may allow the lead pulling tool 214 to pull the lead 100 through the vasculature of the patient to an implantation site in an ITV and/or an intercostal vein of the patient, or to pull the lead 100 to an exit point from an ITV or an intercostal vein to allow coupling to an electrode implantable subcutaneously.

Figure 3A:
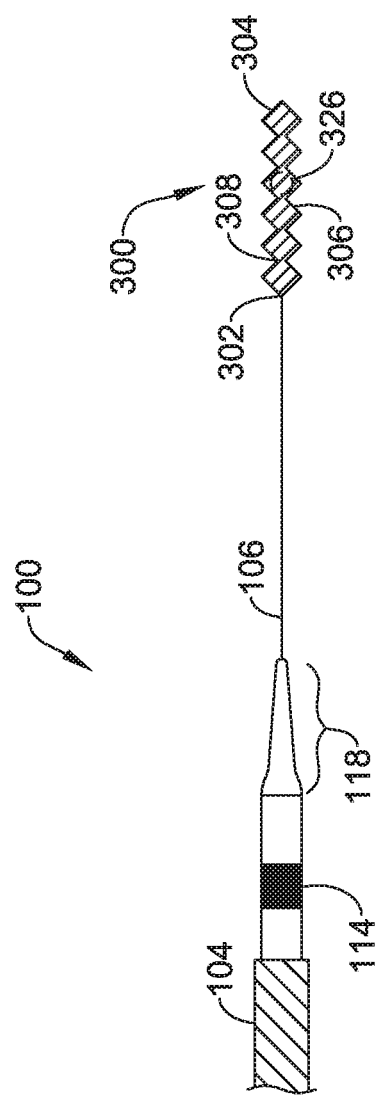
FIGS. 3A-3E illustrate the exemplary lead with another exemplary attachment feature.

FIGS. 3A-3E show the lead 100 with another illustrative attachment feature. For clarity, the attachment feature has been enlarged in FIGS. 3A-3E. According to various embodiments, the attachment feature may have an outer diameter between 0.5 French and 2 French, similar to the distal portion 106. Referring to FIG. 3A, the attachment feature may be an elongated member 300 having a first end 302 and an opposing second end 304. The first end 302 may be coupled to the distal end 120 of the lead 100 by any suitable means or, in other embodiments, the distal end 120 and the elongated member 300 may be one continuous, single, element. In certain embodiments, the elongated member 300 may have straight edges and take on a cylindrical form. However, as shown in FIG. 3A, the elongated member 300 may also taper off at the second end 304. In some cases, the elongated member 300 may have external threads 306 (e.g., "male threads") that extend from an edge 308 of the first end 302 over a sufficient axial distance of the elongated member 300. In some examples, there may be a bore or hole 326 through the elongated member 300. The hole 326 may be configured to receive a fastener therethrough. In some embodiments, the hole 326 may be threaded and configured to receive a screw or another suitable threaded apparatus.

Figure 3B:
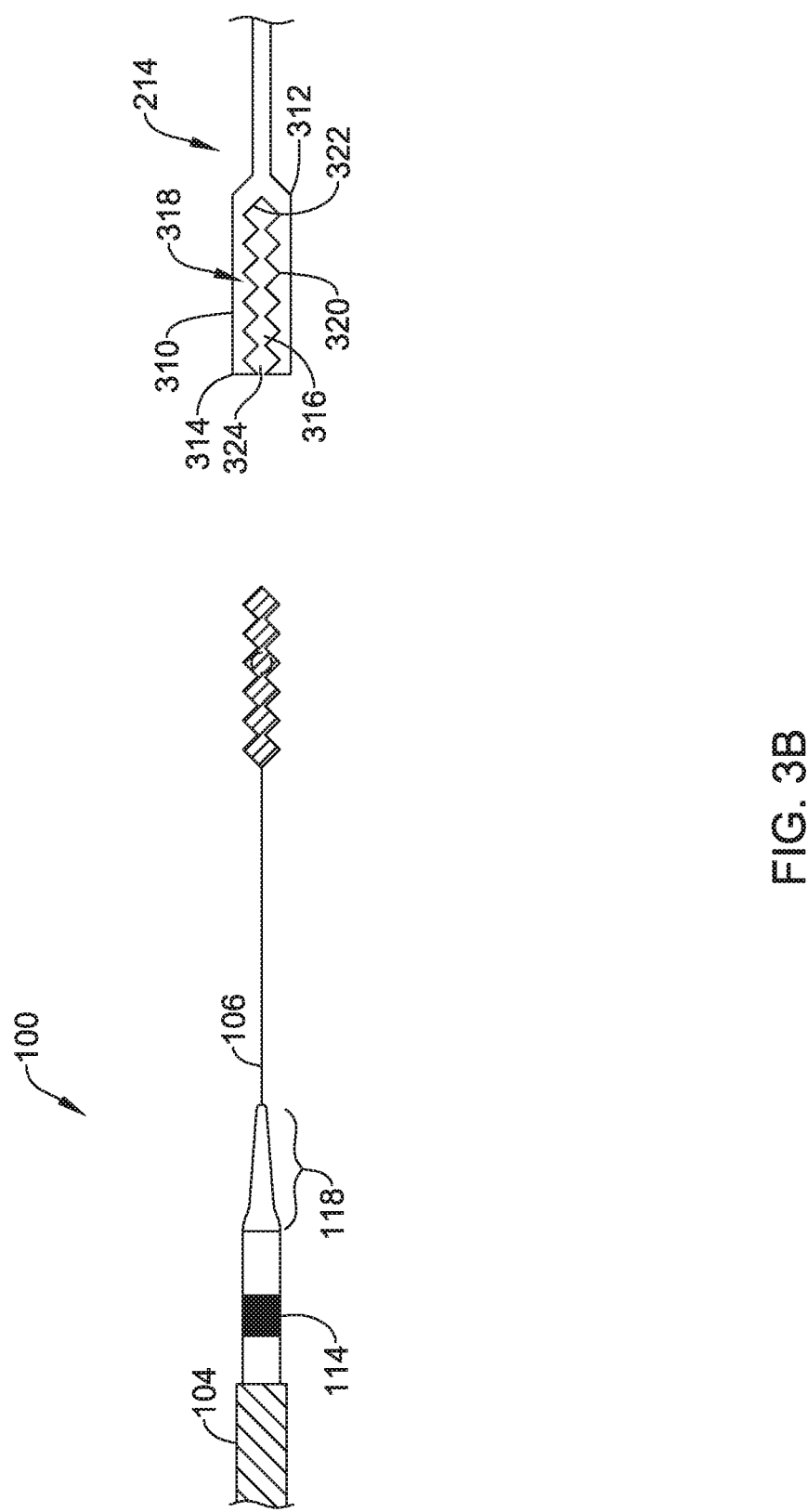

Turning to FIG. 3B, the lead pulling tool 214 may have a proximal tip portion that may be a shell 310 having a first end 312 and an opposing second end 314 (a cross-sectional view of the proximal tip portion 310 is shown in FIG. 3B).

Figure 3C:
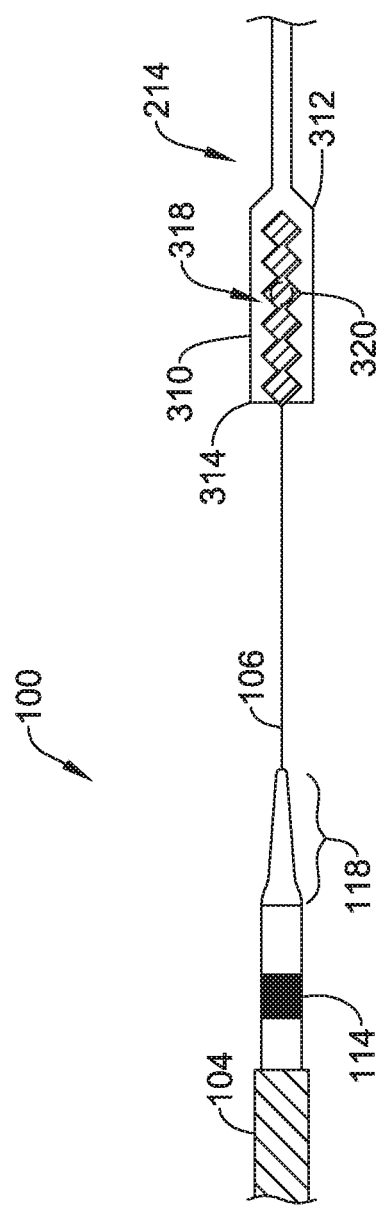

In various embodiments, the shell 310 may have an inner cavity 316. Moreover, an inner wall 318 of the cavity 316 may be comprised of threads 320 (e.g., "female threads") that extend from an edge 322 of the first end 312 over a sufficient axial distance of the inner wall 318. The second end 314 may also have an opening 324 that may be configured to allow the elongated member 300 to enter the cavity 316. In some cases, the external threads 306 of the elongated member 300 may interweave with the threads 320 of the shell 310. As shown in FIG. 3C, as the elongated member 300 moves from the opening 324 to the edge 322 of the first end 312, the elongated member 300 may become increasingly tightened to the lead pulling tool 214. As a result, the lead pulling tool 214 may become coupled to the lead 100. In some examples, the coupling of the lead 100 to the lead pulling tool 214 may allow the lead pulling tool 214 to pull the lead 100 through the vasculature of the patient to an implantation site in an ITV and/or an intercostal vein of the patient, or to pull the lead 100 to an exit point from an ITV or an intercostal vein to allow coupling to an electrode implantable subcutaneously.

Figure 3D:
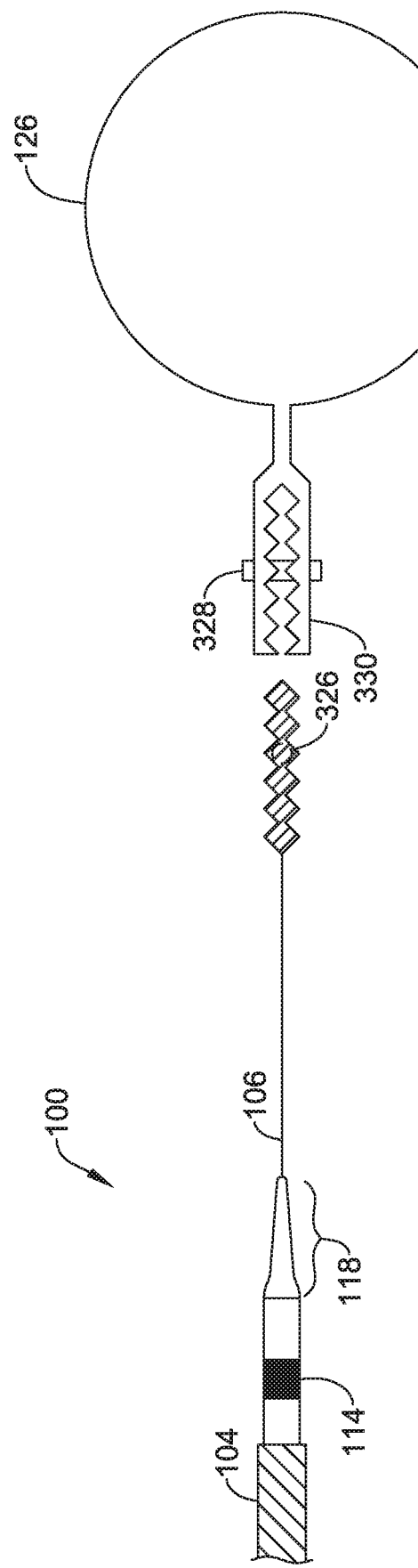
Figure 3E:
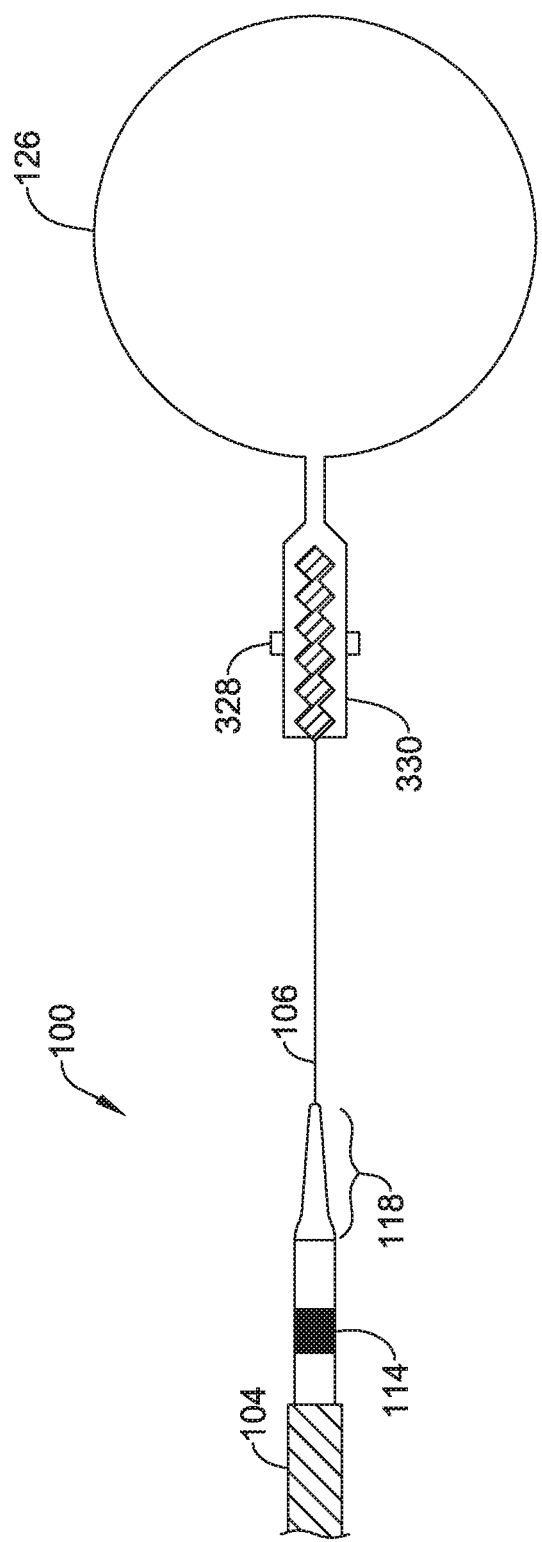

When the lead pulling tool 214 has completed pulling the lead 100, the elongated member 300 may move from the edge 322 of the first end 312 to the opening 324 and the threads of the elongated member 300 may unweave from the threads 320 of the shell 310. As a result, the lead pulling tool 214 may be detached from the lead 100. According to various examples, a shocking element may now be attached to the lead 100. For example, FIG. 3D shows the solid disk electrode 126 (from FIG. 1C) with a connector 330 of similar shape and configuration as the shell 310 of the lead pulling tool 214. However, the disk electrode 126 also includes a screw 328 configured to be place inside the hole 326 of the elongated member 300. As shown in FIG. 3E, when the screw 328 is removed from the connector 330, the connector 330 and the elongated member 300 may be coupled to one another similar to how the elongated member 300 was coupled to the shell 310. In addition, the screw 328 may be passed through the hole 326, securely fastening the lead 100 to the solid disk electrode 126.

Figure 4A:
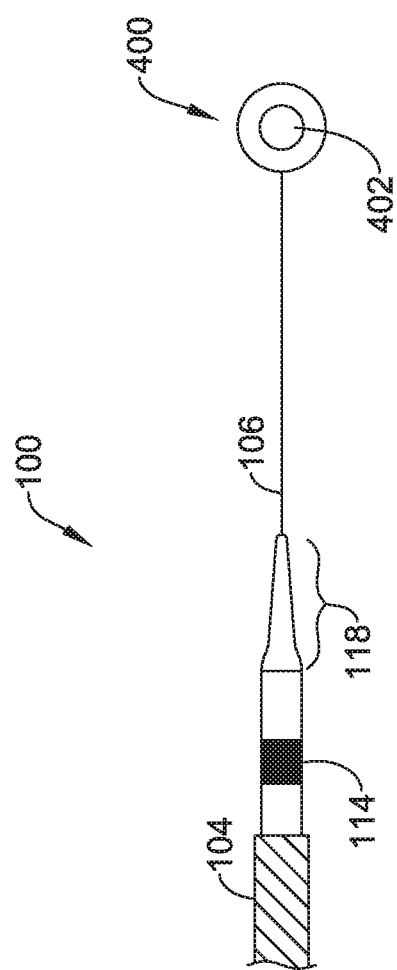
FIGS. 4A-4E illustrate the exemplary lead with another exemplary attachment feature.

FIGS. 4A-4E show the lead 100 with another illustrative attachment feature. For clarity, the attachment feature has been enlarged in FIGS. 4A-4E. According to various embodiments, the attachment feature may have an outer diameter between 0.5 French and 2 French, similar to the distal portion 106. Referring to FIG. 4A, the attachment feature may be a tether retention structure 400. The tether retention structure 400 may be coupled to the distal end 120 of the lead 100 by any suitable means or, in other embodiments, the distal end 120 and the tether retention structure 400 may be one continuous, single, element. The tether retention structure 400 may define an opening 402 configured to receive a hook, tether, fastener or other anchoring mechanism therethrough. In some examples, the opening 402 may be threaded and configured to receive a screw or another suitable threaded apparatus. While the tether retention structure 400 is shown as having a generally "O-shaped" configuration, the tether retention structure 400 may take any shape that provides an enclosed perimeter surrounding the opening 402.

Figure 4B:
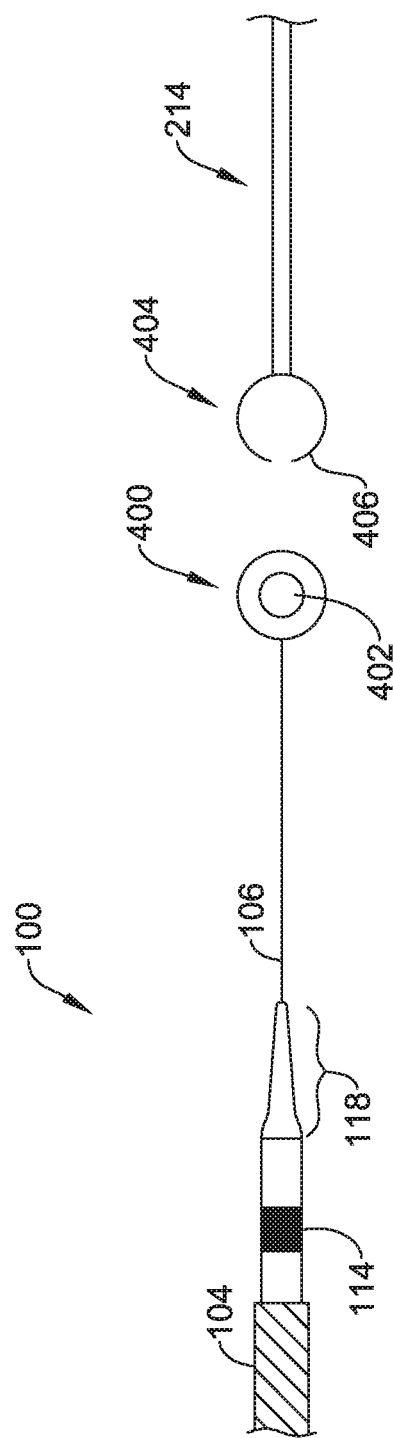

Turning to FIG. 4B, the lead pulling tool 214 may have a proximal tip portion that is an anchoring mechanism 404 and may be configured to pass through the opening 402. In certain embodiments, the anchoring mechanism 404 may have an actuator that opens the anchoring mechanism 404 such that the anchoring mechanism 404 may pass over and under the tether retention structure 400.

Figure 4C:
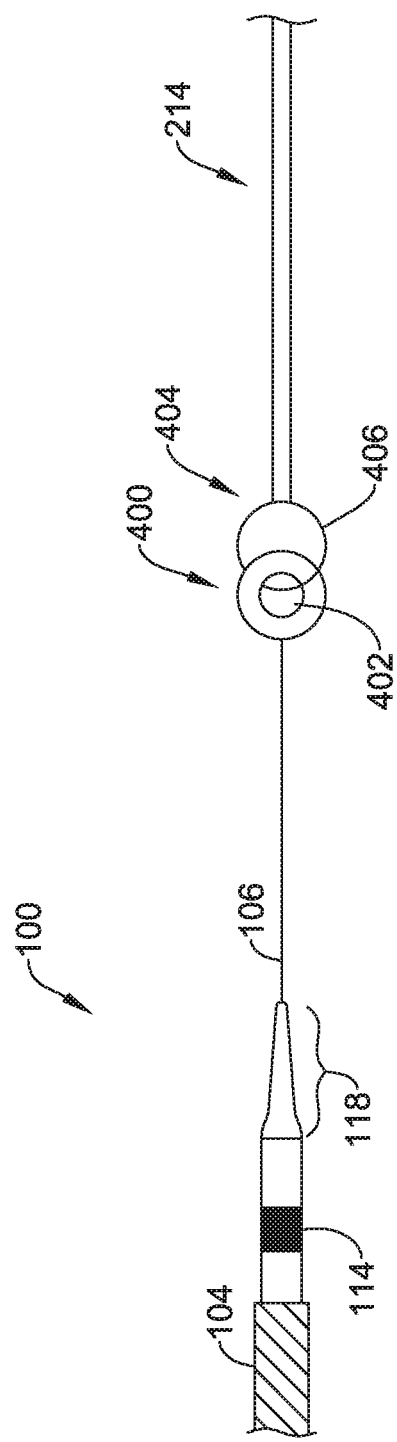

As shown in FIG. 4C, the actuator may then close the anchoring mechanism 404 such that the anchoring mechanism 404 passes through the opening 402. As a result, the lead pulling tool 214 may become coupled to the lead 100. In some cases, the attachment feature may be an anchoring mechanism and the proximal tip portion may be a tether retention structure. In these cases, the pulling tool 214 may be coupled to the lead 100 similar to the coupling just described, but in opposite fashion. In some examples, the coupling of the lead 100 to the lead pulling tool 214 may allow the lead pulling tool 214 to pull the lead 100 through the vasculature of the patient to an implantation site in an ITV and/or an intercostal vein of the patient, or to pull the lead 100 to an exit point from an ITV or an intercostal vein to allow coupling to an electrode implantable subcutaneously.

Figure 4D:
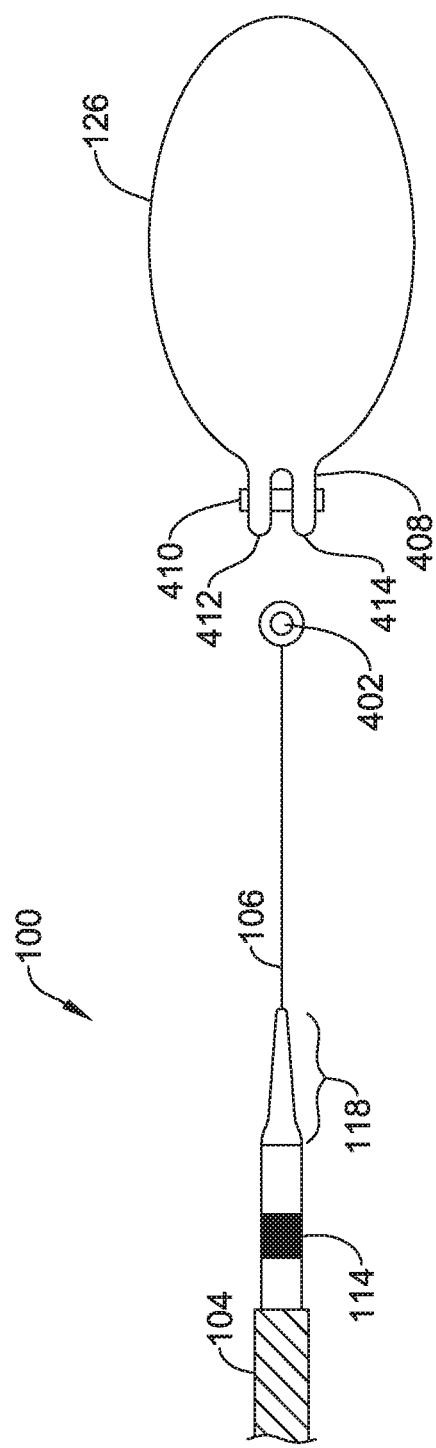
Figure 4E:
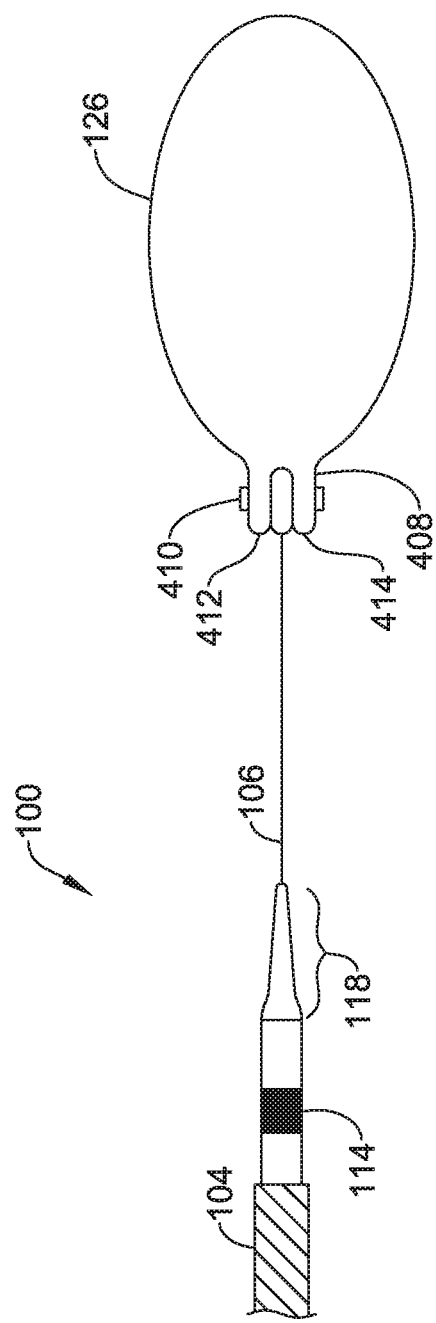

When the lead pulling tool 214 has completed pulling the lead 100, the actuator may open the anchoring mechanism 404 once again and the anchoring mechanism 404 may pass over and under the tether retention structure 400. As a result, the lead pulling tool 214 may be detached from the lead 100. According to various examples, a shocking element may now be attached to the lead 100. For example, FIG. 4D shows the solid disk electrode 126 (from FIG. 1C) with a connector 408 configured to receive the tether retention structure 400. Accordingly, as shown in FIG. 4E, a fastener 410 may first be removed from the connector 408 and the tether retention structure 400 may be slid between a top element 412 and a bottom element 414 of the connector 408. The fastener 410 may then be passed through the opening 402 and securely fasten the lead 100 to the solid disk electrode 126.

Figure 5A:
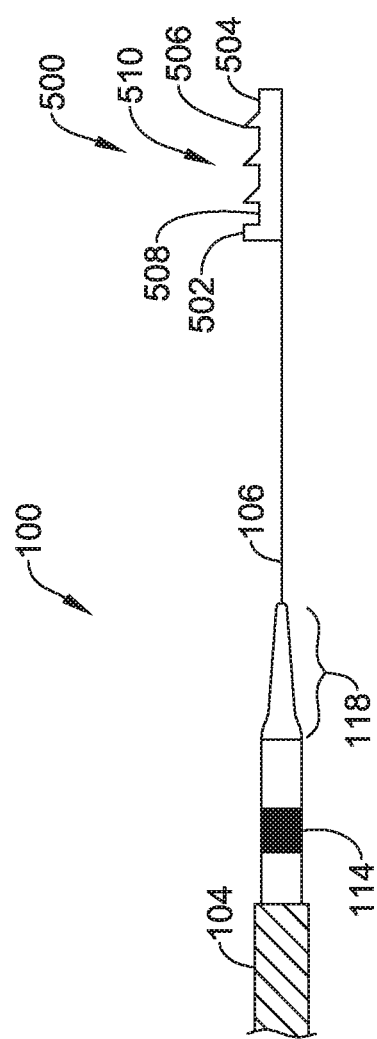
FIGS. 5A-5C illustrate the exemplary lead with another exemplary attachment feature.
Figure 5B:
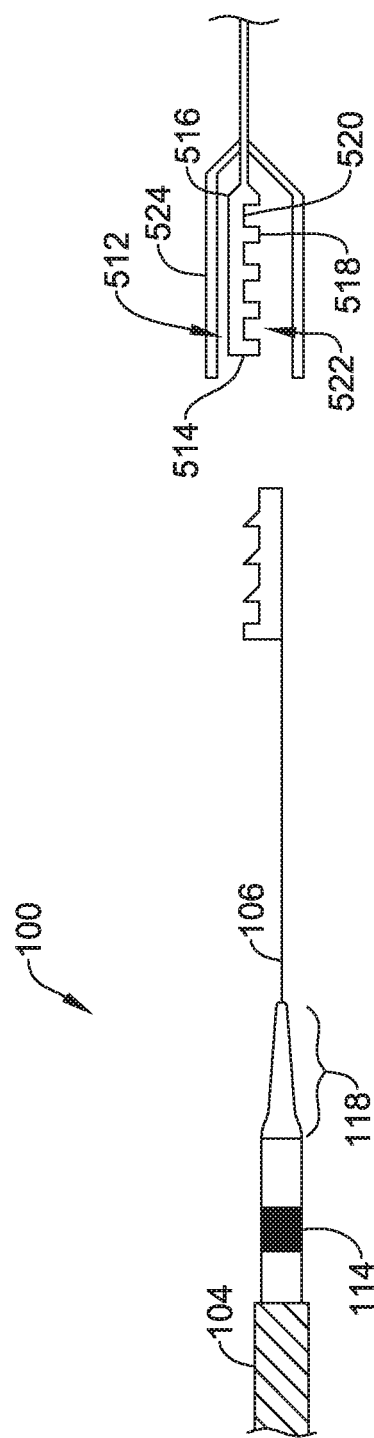
Figure 5C:
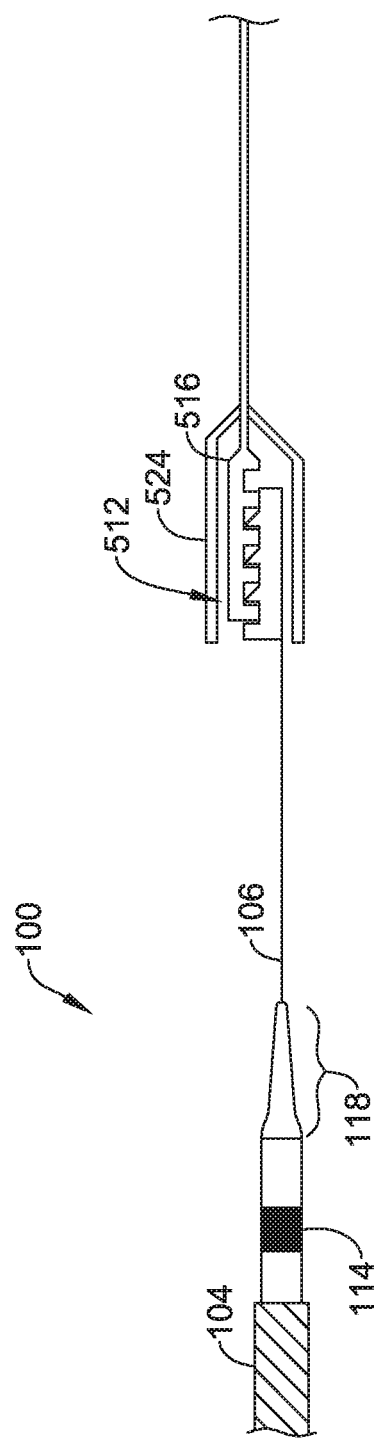

FIGS. 5A-5C show the lead 100 with another illustrative attachment feature. Referring to FIG. 5A, the attachment feature may be a first elongated member 500 having a first end 502 and an opposing second end 504. The first end 502 may be coupled to the distal end 120 of the lead 100 by any suitable means or, in other embodiments, the distal end 120 and the first elongated member 500 may be one continuous, single element. In various embodiments, there may be ridges or hooks 506 and depressions 508 on a top-side of the first elongated member 500.

Turning to FIG. 5B, the lead pulling tool 214 may have a proximal tip portion 512 that may be a second elongated member 512 having a first end 514 and an opposing second end 516. In various embodiments, there may be ridges or hooks 518 and depressions 520 on a bottom-side of the second elongated member 512. In addition, the proximal tip portion may also have an alignment structure 524 surrounding the second elongated member 512. In certain embodiments, the alignment structure 524 may slide along the length of the lead pulling tool 214 to accommodate the coupling action. As shown in FIG. 5C, the first elongated member 500 may pass within the alignment structure 524, underneath the second elongated member 512. The ridges 506 of the first elongated member 500 may then be aligned with the depressions 520 of the second elongated member 512 and the ridges 518 of the second elongated member 512 may be aligned with the depressions 508 of the first elongated member 500. The first elongated member 500 and the second elongated member 512 may then be pressed together. As a result, when the lead pulling tool 214 is pulled in the opposite direction of the lead 100, the ridges 518 of the second elongated member 512 may press against the ridges 506 of the first elongated member 500 allowing the lead pulling tool 214 to pull the lead 100. Furthermore, the alignment structure 524 may be configured to keep the ridges 518 of the second elongated member 512 from sliding off the ridges 506 of the first elongated member 500.

The attachment features, proximal tip portions, and connectors described above are by no means exhaustive. In some cases, the attachment feature, the proximal tip portion, and the connector may include other configurations that facilitate the coupling of the lead 100 to the lead pulling tool 214 and the lead 100 to the shocking element. Delivery of the lead 100 will now be described. In the description, examples will show use of the lead 100 (from FIG. 1A), the lead pulling tool 214 (from FIG. 2B) the tether retention structure 400 (from FIG. 4A), the anchoring mechanism 404 (from FIG. 4B), and the solid disk electrode 126 (from FIG. 1C) with the connector 408 (from FIG. 4D). However, it should be understood that the delivery may be done using any of the attachment features, proximal tip portions, and/or connectors described herein. Moreover, the delivery may be done by any attachment features, proximal tip portions, and/or connectors that allow the lead pulling tool 214 to pull the lead 100 through the vasculature of the patient to an implantation site in an ITV and/or an intercostal vein of the patient.

Figure 6A:
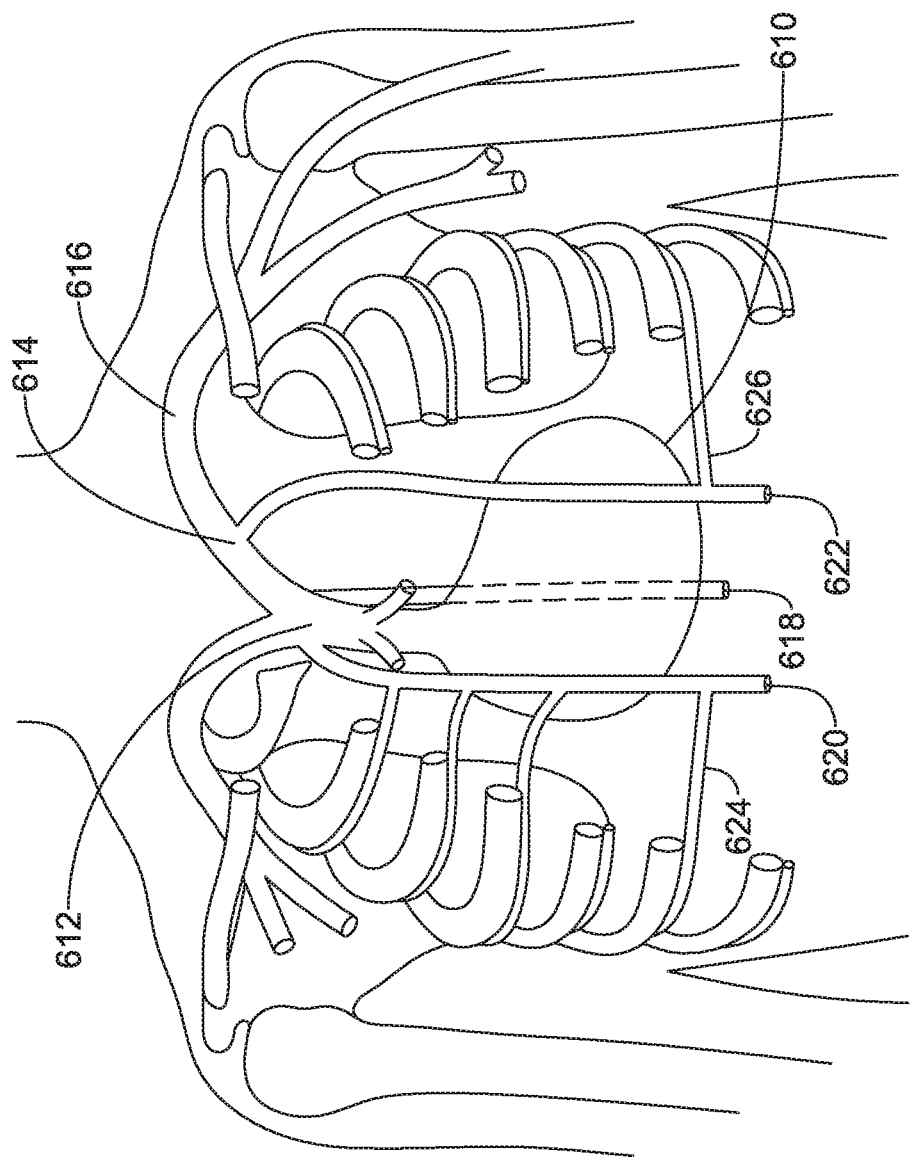
FIG. 6A illustrates the thoracic anatomy including the internal thoracic veins (ITVs)

FIG. 6A illustrates the thoracic anatomy including location of the internal thoracic veins (ITVs) 620, 622. A right intercostal vein 624 may couple to the right ITV 620 and a left intercostal vein 626 may couple to the left ITV 622. The right and left intercostal veins 624, 626 may each run along a costal groove on an inferior portion of a rib. Additionally, an artery (not shown) and a nerve (not shown) may be located inferior (in that order) to the intercostal veins 624, 626 and also run along the costal groove. An outline of the heart is shown at 610, with the superior vena cava (SVC) shown at 612. The brachiocephalic veins 614 couple to the SVC 612 and extend past various cephalic branches (not shown) to the subclavian vein 616. The azygos vein is also shown at 618. As can be seen, the right and left ITV 620, 622 couple to the respective right and left brachiocephalic veins 612, 614.

Figure 6B:
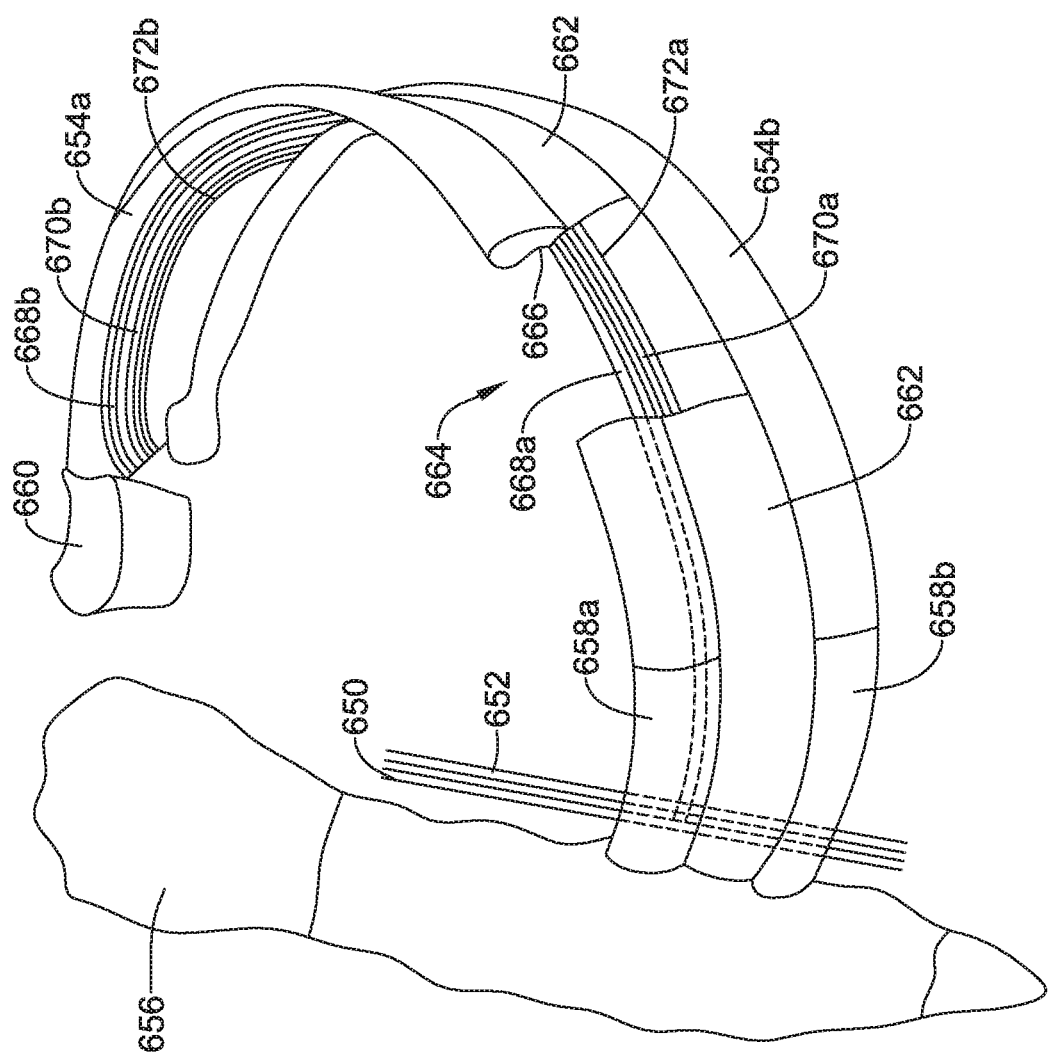
FIG. 6B illustrates another view of the left thoracic anatomy.

FIG. 6B illustrates an alternative view of some of the left thoracic anatomy. The ribs 654a, 654b (collectively, 654) are connected anteriorly to the sternum 656 through costal cartilage 658a, 658b (collectively, 658) and are coupled posteriorly to the spine 660. It should be understood that for clarity, not all of the ribs 654, or other anatomy that may be present, are illustrated. Intercostal muscle 662 extends between the ribs 654. A region of one of the ribs 654a and a portion of the intercostal muscle 662 has been removed at the area generally indicated by arrow 664 to expose the anterior intercostal vein 668a, the anterior intercostal artery 670a, and the anterior intercostal nerve 672a disposed in or adjacent to the costal groove 666. Each rib in the ribcage includes an intercostal vein, artery, and nerve.

The anterior intercostal vein 668a follows the rib 654a laterally and posteriorly to become the posterior intercostal vein 668b. Similarly, the anterior intercostal artery 670a and the anterior intercostal nerve 672a follow the rib 654a laterally and posteriorly to become the posterior intercostal artery 670b and the posterior intercostal nerve, respectively. The left anterior intercostal veins 668a drain to the left ITV 650, shown next to the internal thoracic artery 652. The anterior intercostal vein 668a is shown in phantom under the rib 654a to further illustrate this connection between the ITV 650 and the anterior intercostal vein 668a. While not explicitly shown, the right anterior intercostal veins drain to the right ITV. The posterior intercostal veins 668b drain to the azygos vein system. The superior left posterior intercostal veins drain to the accessory hemiazygos vein, the inferior left posterior intercostal veins drain to the hemiazygos vein and the right posterior intercostal veins drain to the azygos vein.

Each of the ITV, azygos vein, hemiazygos vein, accessory hemiazygos vein, and intercostal veins may be deemed part of the venous vasculature as used herein in several examples.

Figure 7:
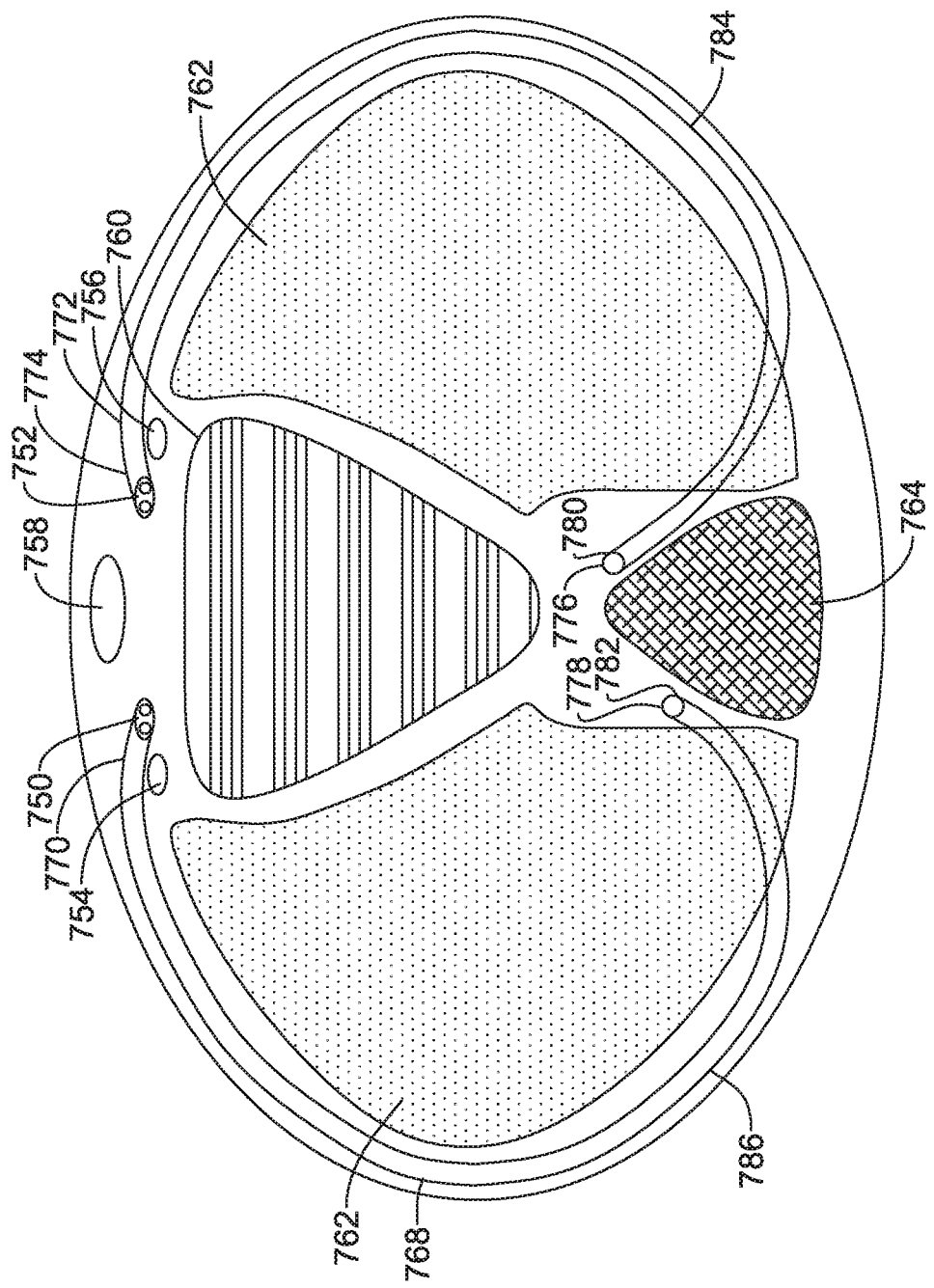
FIG. 7 shows the torso in a section view to highlight the location of the ITVs and other structures.

FIG. 7 shows the torso in a section view to highlight the location of various vascular structures. More particularly, in the example, the left and right ITV are shown at 750, 752, running parallel to and more central of the internal thoracic arteries 754, 756, on either side of the sternum 758. The heart is shown at 760, with the lungs at 762 and spinal column at 764. The ITV 750, 752 lie beneath the ribs but outside and separate from the pleurae of lungs 762. The ribs are omitted in the drawing in order to show the intercostal veins. A left anterior intercostal vein 768 runs along the inferior portion of a rib and couples to the left ITV 750 at junction 770, forming an ostium at the point where the left anterior intercostal vein 768 flows into the left ITV 750. Additionally, a right intercostal vein 772 runs along the inferior portion of another rib and couples to the right ITV 752 at junction 774, forming an ostium at the point where the anterior intercostal vein 772 flows into the right ITV 752.

An azygos vein and a hemiazygos vein are shown at 776, 778, running parallel to and on either side, more or less, of the spinal column 764. The azygos vein 776 and the hemiazygos vein 778 also lie beneath the ribs but outside and separate from the pleurae of lungs 762. The left posterior intercostal vein 786 couples to the hemiazygos vein 778 at a junction 782, forming an ostium at the point where the intercostal vein 768 flows into the hemiazygos vein 778. Additionally, the right posterior intercostal vein 784 couples to the azygos vein 776 at a junction 780, forming an ostium at the point where the intercostal vein 772 flows into the azygos vein 776.

Figure 8B:
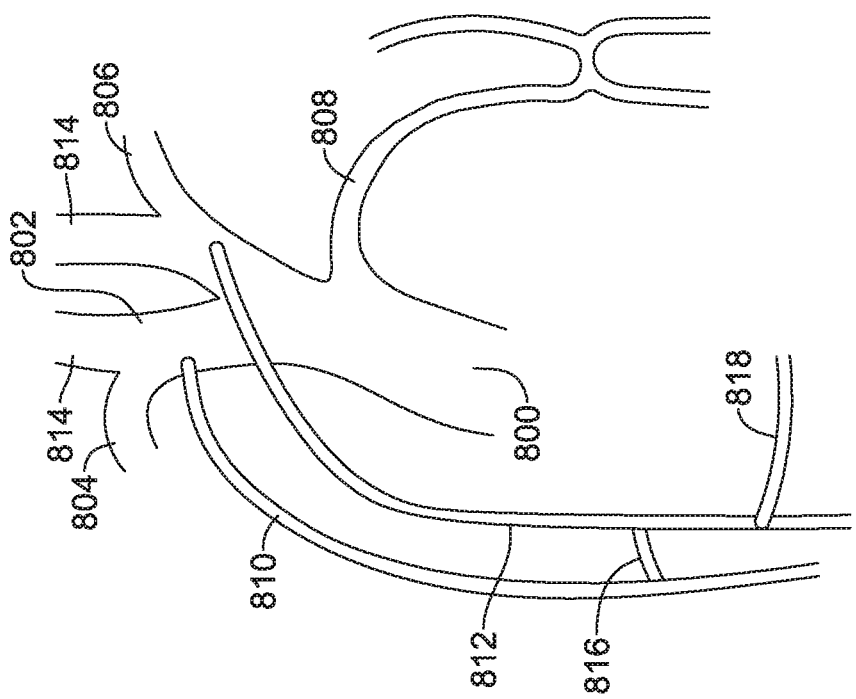
FIGS. 8A-8B show the ITVs and linked vasculature in isolation.
Figure 8A:
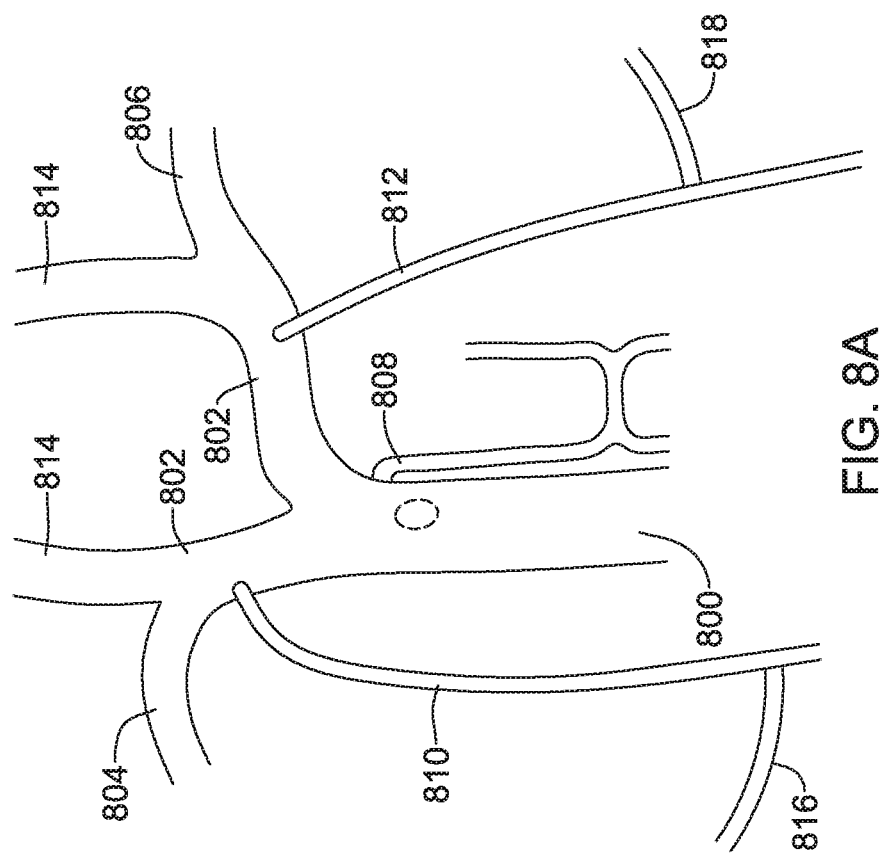

FIGS. 8A-8B show the ITV and linked vasculature in isolation. FIG. 8A is an anterior view of selected portions of the venous structure of the upper torso, and FIG. 8B is a lateral view of the same. The SVC is shown at 800, with the brachiocephalic veins 802 splitting at the upper end of the SVC. The right subclavian vein is at 804, and the left subclavian vein is at 806. The azygos vein is included in the illustration at 808, extending off the posterior of the SVC, and running inferiorly posterior of the heart as can be understood from the lateral view of FIG. 8B. The right and left ITV are shown at 810, 812. These each branch off at a location that is considered part of the brachiocephalic veins 802. Selected right and left intercostal veins are shown at 816, 818. There are left and right intercostal veins along the lower margin of each of the ribs. In several embodiments the intercostal veins of the $5^{th}$, $6^{th}$, or $7^{th}$ ribs are proposed for implantation of a lead with access through the ITV to the intercostal vein or from the intercostal vein to the ITV. In one example, the intercostal vein of the $6^{th}$ rib is used for implantation. In other examples, implantation may be more superior or inferior than these locations, as desired. The intercostal veins branch off at a location of the right and left ITV's and continue to run along a coastal groove of an inferior portion of a ribs. The internal jugular veins are also shown at 814.

As shown above in FIG. 7, the intercostal veins 816, 818 wrap around to the azygos, hemiazygos or accessory hemiazygos veins, depending on which of left or right, and how superior or inferior the intercostal vein 816, 818 is. In some examples, an intercostal vein 816, 818 may be used to access the posterior of the patient for implant on the back of the patient of a lead for sensing or therapy delivery, or even to access still further the azygos, hemiazygos, or accessory hemiazygos veins, if desired, for implantation of a lead, electrode, or device.

FIGS. 9A-9D show access to and implantation of the lead 100 in the ITV 958. Starting with FIG. 9A, the heart is shown at 950 with the SVC at 952 and the brachiocephalic vein right branch at 954 and left branch at 956. Access to the subclavian vein 960 is shown at 970 using standard access techniques known in the art for implanting traditional transvenous pacemakers and defibrillators. For example, the Seldinger technique may be used by creating a puncture with a hollow needle or trocar, for example under ultrasound guidance, introducing the lead pulling tool 214 (e.g., a guidewire) through the needle, removing the needle, and then inserting an introducer sheath 972, which may have a valve at its proximal end, over the lead pulling tool 214. Other venipuncture or cutdown techniques may be used instead. Other vessels may be accessed instead of the subclavian vein using similar techniques including, for example, the jugular, cephalic, or axillary veins.

Into the access at 970, an introducer sheath 972 is inserted and advanced to a location to place its distal tip 980 near the ostium of the left ITV 958. Contrast injection may be useful to visualize the ITV structures and the ostia of the ITVs. A guide catheter 974 and a distal end 984 of a lead pulling tool 214 may then be introduced through the introducer sheath 972. In other examples, a shorter introducer sheath may be used, with the guide catheter 974 used to traverse the distance to the relevant ostium.

In certain embodiments, the lead pulling tool 214 may be a guidewire and may be the same as used in gaining initial access 970 (if one is used to gain access 970), or may be a different guidewire. In an example, the lead pulling tool 214 is preloaded in the guide catheter and both are introduced at the same time until the guide catheter 974 is at a desired location relative to the ostium of the selected ITV. The distal end 984 of the lead pulling tool 214, which may be deflectable or steerable, can then be used to enter the left ITV 958 through the ostium thereof, passing down into the left ITV 958.

The lead pulling tool 214 passing into the ITV from a superior position will need to pass through the valves of the ITV in a direction counter to their natural tendency (the valves in the veins prevent blood from flowing inferiorly). For an example where the lead pulling tool 214 passes unsupported by a guide catheter into the ITV from a superior position, the lead pulling tool 214 may be a preferably stiff guidewire. In some examples, the lead pulling tool 214 may be at least two guidewires that are used, a first more flexible and steerable guidewire to obtain initial access via the ostium of the ITV, and a second, stiffer guidewire that is sufficiently pushable to allow passage through the valves in the ITV.

In some examples, the guide catheter 974 is introduced first and the lead pulling tool 214 is introduced next. For example, a steerable or curved guide catheter 974 may traverse the introducer sheath 972 to its distal end 980 and then, using steering of the guide catheter or a precurved structure of the guide catheter, would then turn as shown at 982 to enter the left ITV 958. The lead pulling tool 214 may then be introduced through the guide catheter 974 and advanced into the left ITV 958.

Figure 9A:
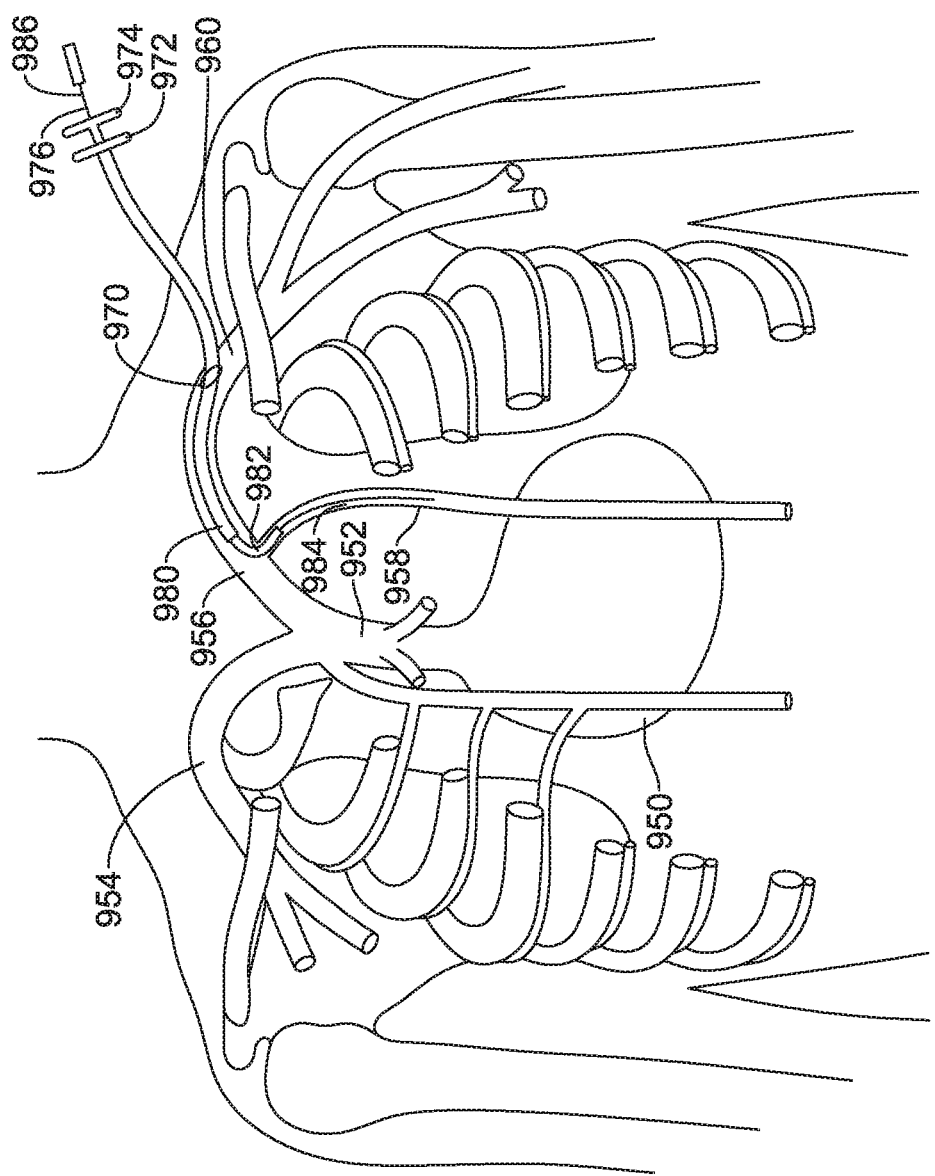
FIGS. 9A-9D show access to and implantation of a lead in the left ITV.
Figure 9B:
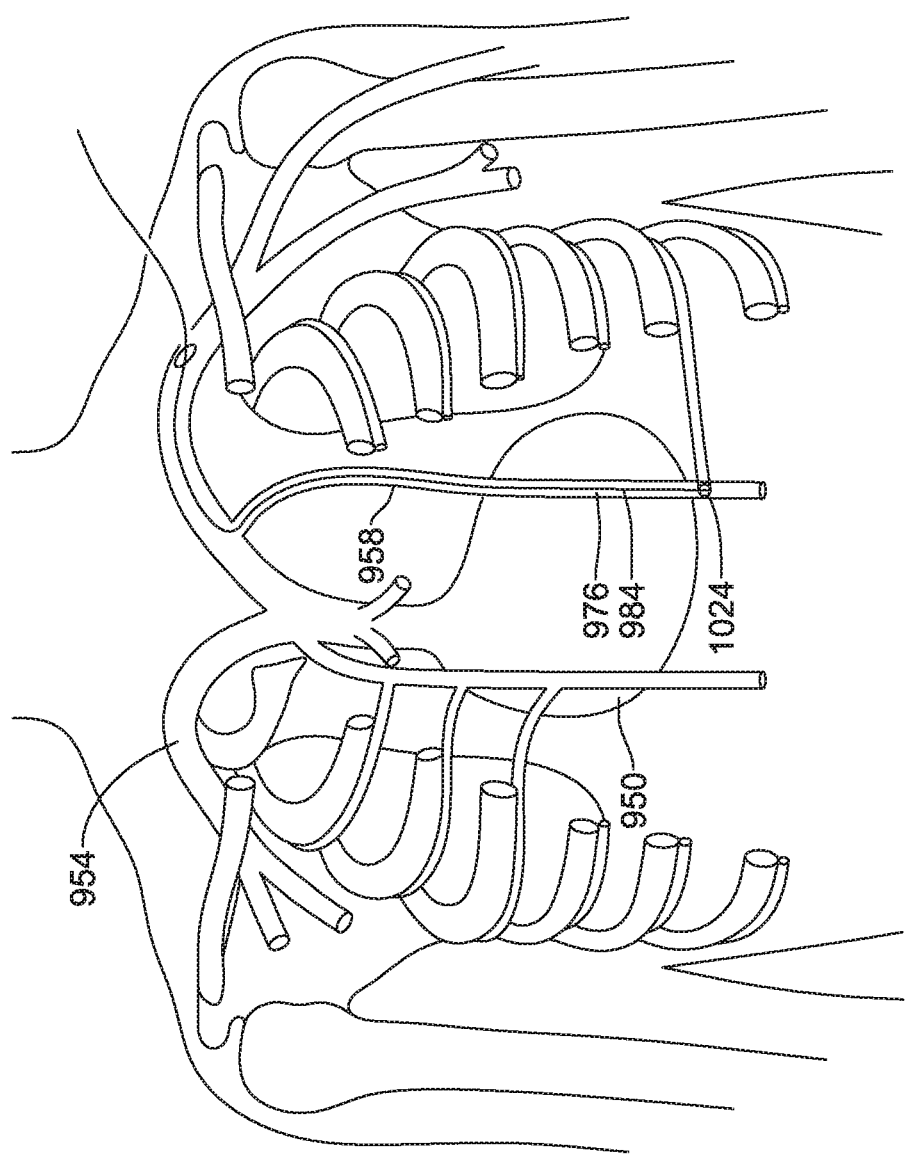

FIG. 9B shows the distal end 984 of the lead pulling tool 214 in the ITV 958. In certain cases, the ITV 958 may have a diameter on the order of 3 mm or greater and in addition to the anatomy surrounding the ITV, it is also recognized that the particular body characteristics from patient to patient may vary including, for example, any venous abnormality, scarring in the area (such as related to any prior sternotomy or the like) as well as the body habitus (overweight or underweight patients). As a result, locating the ITV 958 may be difficult. In some cases, the presence of the lead pulling tool 214 inside the ITV may help disclose the location of the ITV 958 and increase the accuracy of establishing an external access 1024.

For example, in some instances, the lead pulling tool 214 may be a radiopaque guidewire. The lead pulling tool 214 may be instead a stylet, a hypotube, or a catheter having sufficient column strength to allow pushing through blood vessels to desired position, and further with sufficient strength to allow pulling of a lead as described further below. In other cases, a radiopaque material may be placed over the lead pulling tool or a portion thereof.

When the lead pulling tool 214 is inside the ITV 958, the lead pulling tool 214 may then be visualized, for example, using x-ray or fluoroscopy. An individual (e.g., a physician) may then observe the lead pulling tool 214 and adjust the lead pulling tool 214 inside the ITV 958, if needed, to a desired location. Once the lead pulling tool 214 is at the desired location, the proper external access 1024 position (e.g., near the end of the distal end of the lead pulling tool 214 inside the ITV 958 or inside the superior epigastric vein) may be identified. For instance, the physician may use a fluoroscope image to identify the lead pulling tool 214 and place forceps in the view range of the fluoroscope to get a surface position of the lead pulling tool 214 and thus, establish the external access 1024 position. In another embodiment, fluoroscope imaging may be used to identify the lead pulling tool 214 and an x-ray may be used to identify the xiphoid, and the external access 1024 position may be based on the location of the lead pulling tool 214 and the location of the xiphoid.

In some examples, instead of an x-ray, ultrasound imaging may be used to identify the location of the lead pulling tool 214 near the xiphoid. In some examples, fluoroscope imaging may not be used and ultrasound imaging may be used to identify the lead pulling tool 214 and the physician may use an ultrasound needle in the view range of the ultrasound to establish the position of the lead pulling tool 214 and thus, establish the external access 1024 position relative to the ultrasound needle. In some cases, an element may be added to the lead pulling tool such as an ultrasound transducer, a sealed air-filled tube, or another element having dramatic density change that the ultrasound may be able to detect against standard body tissue.

In still further embodiments, a special lead pulling tool 214 may be used that discloses its position in some shape or form in the ITV 958 that enables the physician to establish the external access 1024 position. If desired, an illuminating element such as an LED may be positioned at or near the distal tip of the lead pulling tool 214 to allow ready transcutaneous visualization thereof. These are just some examples of how the lead pulling tool 214 may be used to establish the external access 1024. In other embodiments, the lead pulling tool 214 may be used in conjunction with other conventional locating or visual techniques known by those skilled in the art.

Figure 10:
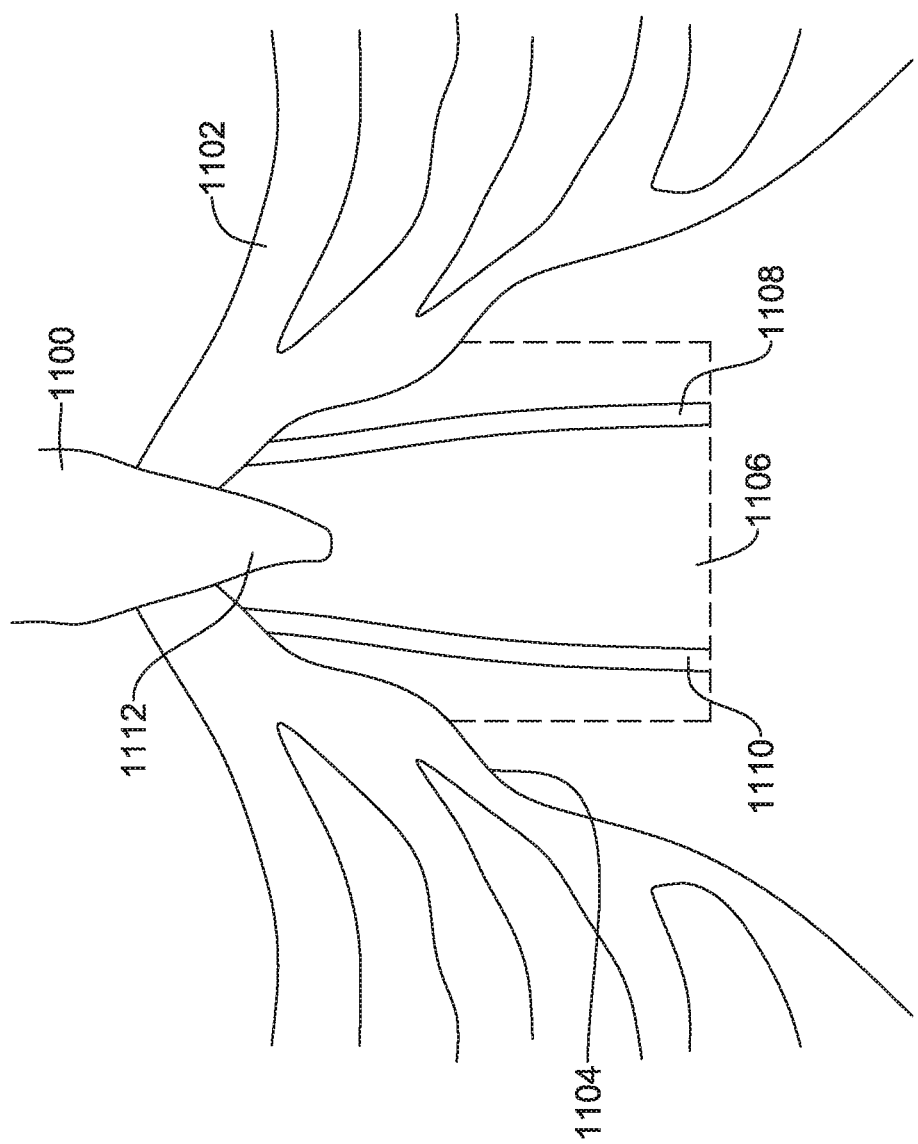
FIG. 10 shows in close view a location inferior to the lower rib margin where the ITV may be accessed inferiorly via the superior epigastric vein.

FIG. 10 illustrates in close view of a location inferior to the lower rib margin where the superior epigastric vein may be accessed. This region may be referred to as the inferior thoracic aperture. The patient anatomy is shown in part including the sternum 1100 and ribs 1102, with the lower rib margin at 1104. A cutout area is shown at 306 in order to illustrate the approximate location for accessing the right or left ITV using the superior epigastric veins. As used herein, the "ITV" is the name applied for the vein while it runs beneath the chest, that is, superior to the lower margin of the ribs. Inferior of this location, the blood vessel is referred to (at least in this description) as the superior epigastric vein. The left superior epigastric vein is shown at 1108, and the right superior epigastric vein is shown at 1110. In order to access either vein 1108, 1110, a physician may use the "visualization" (fluoroscopy, ultrasound, or visual) of the lead pulling tool 214 to obtain external access into the desired vein 1108, 1110 on the desired side of the xiphoid 1112.

Figure 9C:
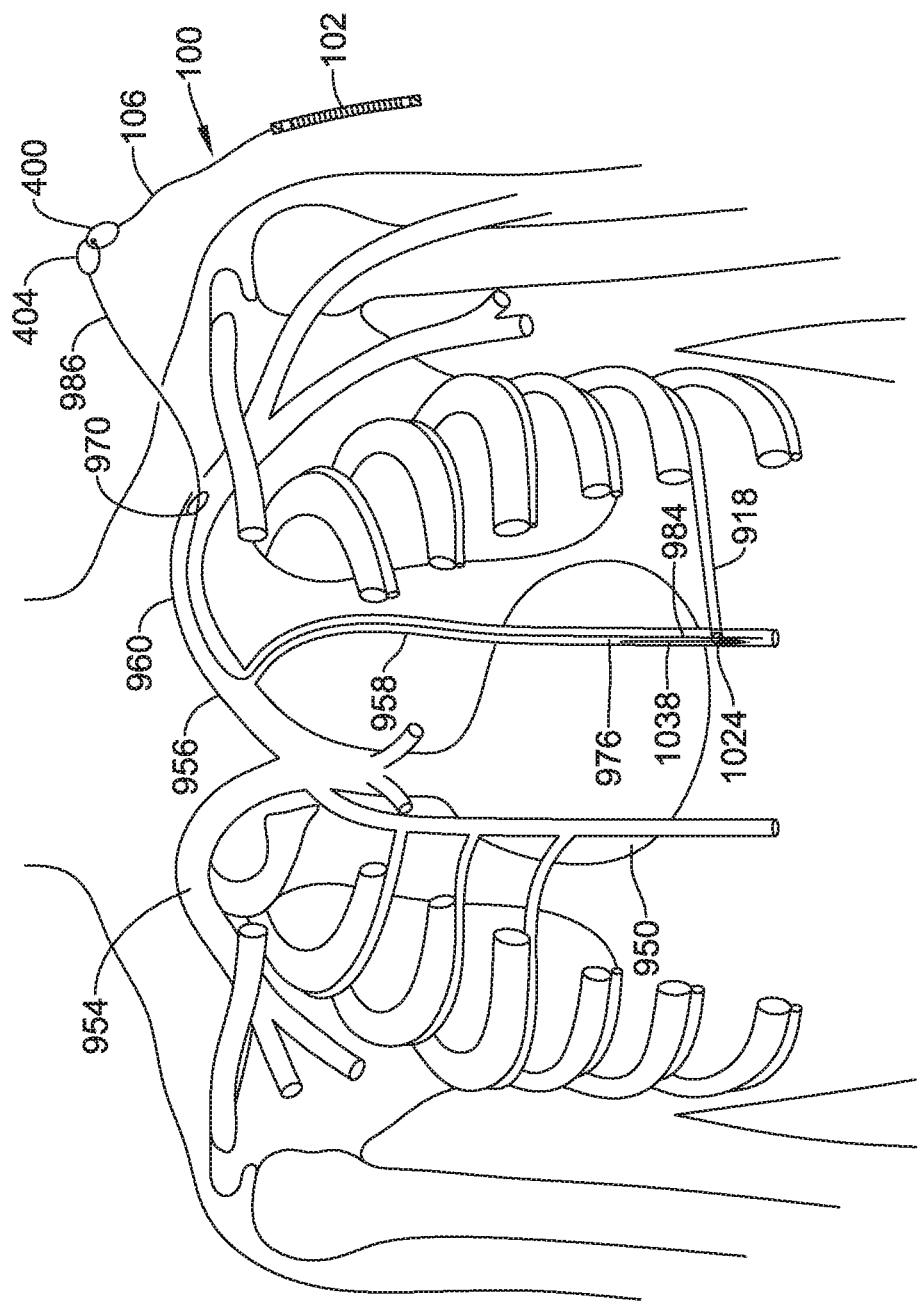

In certain embodiments, as shown in FIG. 9C, access to the distal end 984 of the lead pulling tool 214 may be obtained through the external access 1024. In some cases, the proximal end 986 of the lead pulling tool 214 may include the anchoring mechanism 404. In some cases, the distal portion 106 of the lead 100 may include the tether retention structure 400 that may be configured to attach or couple to the anchoring mechanism 404.

Once the anchoring mechanism 404 of the lead pulling tool 214 is attached to the tether retention structure 400, advancement to the ITV 958 may be achieved by pulling the distal end 984 of the lead pulling tool 214 from the external access 1024 location, as shown by arrow 1038, and drawing the lead 100 from the access point 970, into the subclavian vein 960, to the brachiocephalic vein 956, through the ostium of the ITV 958, and advancing the tether retention structure 400 of the lead 100 to the external access 1024 location to externalize the retention structure 400. When the tether retention structure 400 is at the external access 1024 location, the tether retention structure 400 may be detached from the anchoring mechanism 404. An introducer sheath may then be used at the external access 1024 location to position the lead 100 at the desired level in the ITV 958. In certain embodiments, the proximal portion 102 of the lead 100 may have the coupler 110 configured to attach to an implantable pulse generator.

Figure 9D:
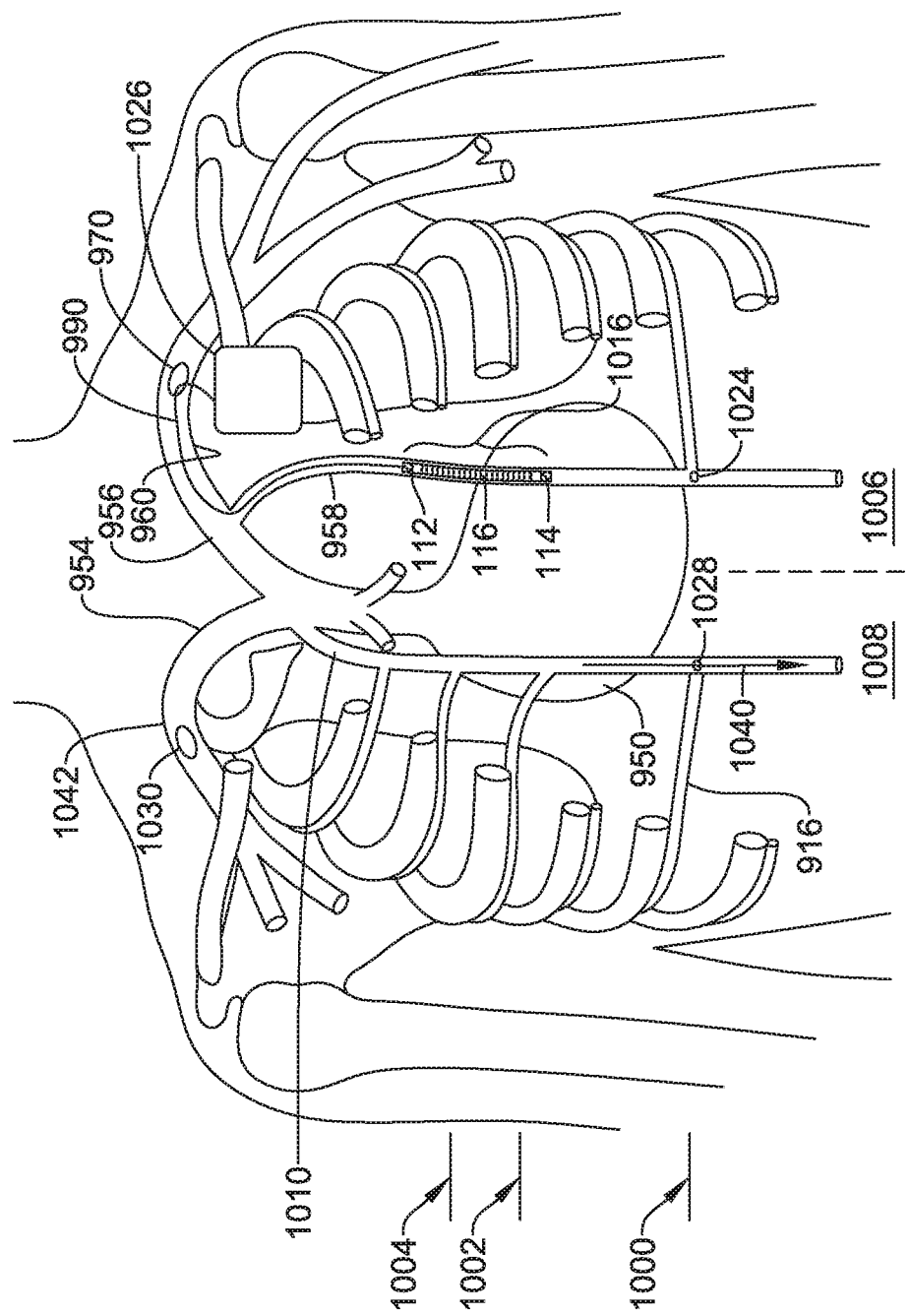

FIG. 9D shows implantation of an implantable cardiac stimulus system. The system includes an implantable pulse generator 1026 which may be placed in the subclavicular location shown (or any other suitable position, as desired). In some cases the implantable pulse generator 1026 may be placed at the high-pectoral or traditional transvenous position. In some cases, the implantable pulse generator 1026 may be placed at approximately the left axilla. For example, the implantable pulse generator 1026 may be placed at the anterior axillary line, the midaxillary line, or in the posterior axillary line. The implantable pulse generator 1026 may also be placed still more posterior beneath the lattisimus dorsi, using a reported method in Kondo et al., "Successful Intermuscular Implantation of Subcutaneous Implantable Cardioverter Defibrillator in a Japanese Patient With Pectus Excavatum." Journal of Arrhythmia, 2016, 10.1016.

According to various embodiments, the coupler 110 of the proximal portion 102 of the lead 100 may be connected to a wire 990 or another suitable conductor that extends from the ITV 958, into the brachiocephalic vein 956, to the subclavian vein 960, through the access point 970 and attaches to the implantable pulse generator 1026. As described in regard to FIG. 1A, the lead 100 may include two sensing/pacing electrodes 112 and 114 and at least one coil electrode 116. The electrodes 112, 114, and 116 may serve as therapy delivery electrodes. As such there may be multiple therapy vectors such as between coil 112 and 114, between either of electrodes 112 and 114 and the canister 1026, or between a combination of two of the three therapy electrodes 112, 114 and canister 1026, and the third such electrode, such as by linking coils 112 and 114 in common as the anode or cathode relative to the canister 1026.

In certain embodiments, the electrodes 112, 114, and 116 may be a plurality of ring electrodes. Electrode 114 may also or instead be a tip electrode. Electrodes 112 and 114 may serve as sensing electrodes. The coil electrode 116 may also serve as a sensing electrode. These various electrodes may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, and/or US PG Patent Application Pub. Nos. 20170112399, 20170113040, 20170113050, and 20170113053, the disclosures of which are incorporated herein by reference.

In addition, one or more of the electrodes 112, 114, and 116 may be used for therapy delivery. In an example, defibrillation therapy may use coils 112 and 114 coupled in common as the opposing pole to the canister 1026, while pacing therapy may use coil 116 as opposing electrodes for post-shock pacing therapy, with a still difference combination of electrodes used to provide ventricular pacing therapy for example by pacing between coil 116 and tip electrode 114.

Line 1002 is provided, illustratively, to separate the atria and ventricles. The lead 100 may be placed as shown such that the distal electrode 114 is about level with the ventricles, and the proximal electrode 112 is about level with the atria, if desired. In some examples fewer or different electrodes may be provided on the lead 100 such as by excluding one or the other of the electrodes 112 or 114.

Line 1004 is provided to indicate the top of the heart, with the apex or bottom of the heart marked at 1000. In some examples, one or more electrodes on the lead 100 are provided at or inferior to the apex 1000, or at or superior to the top 1004 of the heart. In the example shown, on the other hand, the electrodes are located generally between the apex 1000 and top 1004 of the heart.

The illustration shown in FIG. 9D places the lead on the left side 1006 of the patient. In other examples, the right side 1008 of the patient may instead or in addition be accessed, including the right ITV 1010. Access to the right ITV 1010 may be achieved by advancing the lead pulling tool 214 in a similar manner as described in regard to FIG. 9A. However, in this embodiment, the lead pulling tool 214 is advanced from the left subclavian access 970, across to the ostium of the right ITV 1010. Alternatively, access to the right ITV may be achieved as shown by entering a right subclavian vein access point 1030 in a mirror image procedure of that used to obtain the left subclavian access 970. In either example, once the distal end 984 of the lead pulling tool 214 is in the ITV 1010, the lead pulling tool 214 may be located and an external access 1028 may be established.

Once the anchoring mechanism 404 of the lead pulling tool 214 is attached to the tether retention structure 400 of the lead 100, advancement to the ITV 1010 may be achieved by pulling the distal end 984 of the lead pulling tool 214 from the external access 1028, as shown by arrow 1040, and drawing the lead 192 from the access point 970, into the subclavian vein 960, to the brachiocephalic vein 956, through the ostium of the right ITV 1010, and advancing the tether retention structure 400 of the lead 100 to the external access 1028 to externalize the retention structure 400. When the tether retention structure 400 is at the external access 1028, the tether retention structure 400 may be detached from the anchoring mechanism 404. An introducer sheath may then be used at the external access 1028 location to position the lead 100 at the desired level in the ITV 1010. Alternatively, advancement to the ITV 1010 may be achieved by pulling the distal end 984 of the lead pulling tool 214 from the external access 1028, as shown by arrow 1040, and drawing the lead 100 from the access point 970, into the subclavian vein 960, to the brachiocephalic vein 954, through the ostium of the right ITV 1010, and advancing the tether retention structure 400 of the lead 100 to the external access 1028 to externalize the retention structure 400. When the tether retention structure 400 is at the external access 1028, the tether retention structure 400 may be detached from the anchoring mechanism 404. An introducer sheath may then be used at the external access 1028 location to position the lead 100 at the desired level in the ITV 1010.

In an alternative or addition to the illustration of FIG. 9D, an additional subcutaneous patch electrode may be provided by, for example, tunneling from the canister 1026 to an additional location such as the left axilla. If desired, a patch electrode may be attached to a lead as shown in the above FIGS. 1A-1F, 2A-2C, 3A-3E, 4A-4E, and/or 5A-5C, such that a thin lead can be subcutaneously placed from the location of the patch electrode to the location of the canister.

Figure 9E:
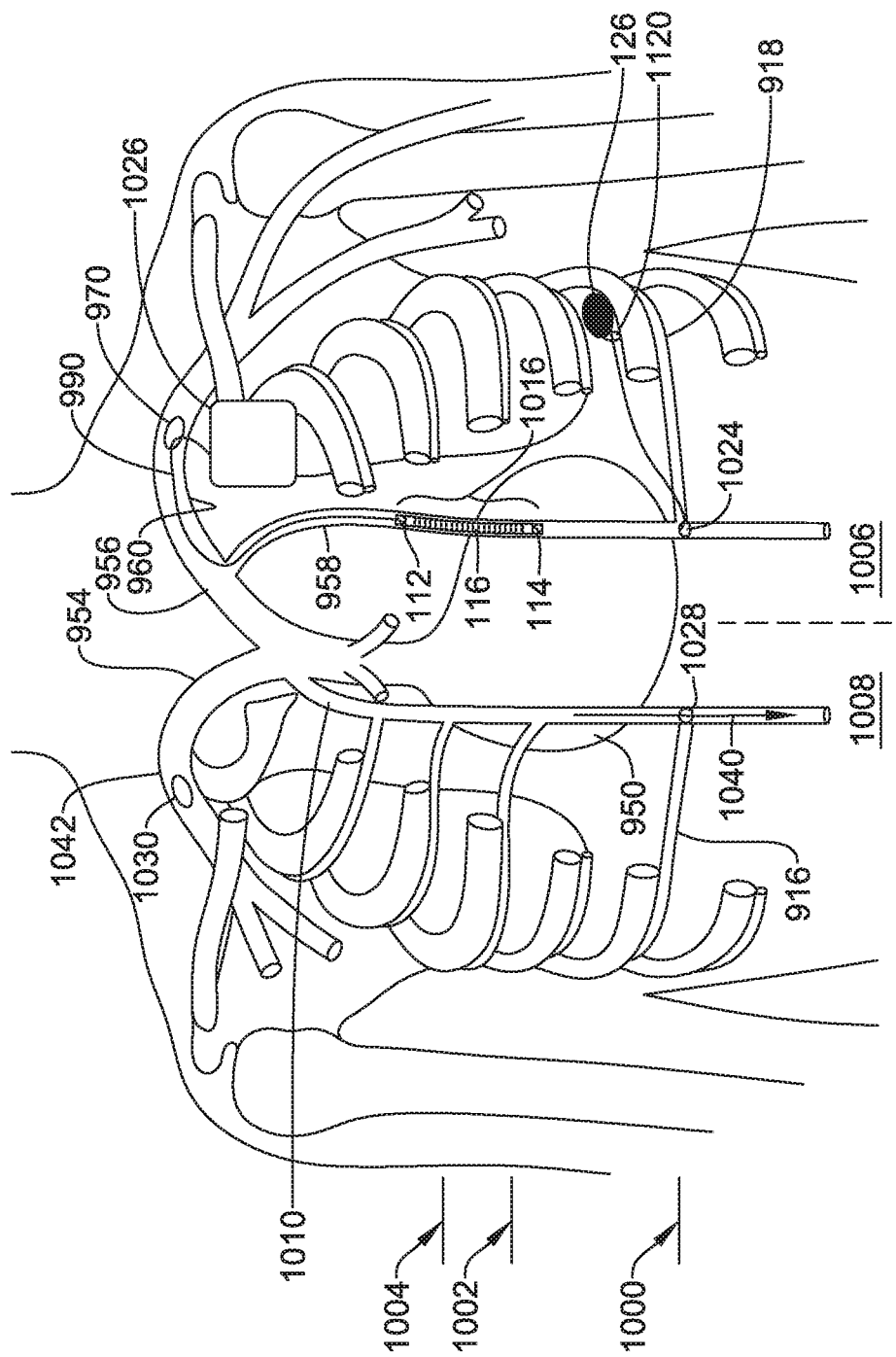
FIG. 9E shows another implantation of a lead in the left ITV.

FIG. 9E shows implantation of another implantable cardiac stimulus system. The system shown in FIG. 9E may be configured and operate similar to the system shown in FIG. 9D. In addition the system shown in FIG. 9E may also include the solid disk electrode 126 which may be placed in the axillary position of the patient (or any other suitable position, as desired. Implantation of the cardiac stimulus system may be performed similar to implantation of the cardiac stimulus system described in FIGS. 9A-9C and shown in FIG. 9D. Additionally, to implant the solid disk electrode 126, when the tether retention structure 400 is at the external access 1024 location, the tether retention structure 400 may optionally be detached from the anchoring mechanism 404 at the external access 1024 location and a suture sleeve may optionally be threaded over the distal portion 106 of the lead 100 for later attachment at the external access 1024. Furthermore, the tether retention structure 400 or the distal end 984 of the lead pulling tool 214 may be tunneled subcutaneously using standard tunneling methods to a left lateral position (e.g., an axillary position) of the patient. Cut-down methods may then be used to create a second external access 1120. The tether retention structure 400 may then either be tunneled to or pulled to the second external access 1120. If the anchoring mechanism 404 has not already been detached from the tether retention structure 400, the second external access 1120 may then be used to externalize the tether retention structure 400 and detach the anchoring mechanism 404 from the tether retention structure 400. The connector 408 of the solid disk electrode 126 may then be attached to the tether retention structure 400 and the second external access 1120 may be used to implant the solid disk electrode 126 at the left lateral position, as shown in FIG. 9E, and the second external access 1120 may be closed.

The illustration shown in FIG. 9E places the lead 100 on the left side 1006 of the patient. In other examples, the right side 1008 of the patient may instead or in addition be accessed, including the right ITV 1010. Implantation of the lead 100 in the right ITV 1010 may be done using the same procedure described above for the system in FIG. 9E. However, in this embodiment, the lead pulling tool 214 is advanced from the left subclavian access 970, across to the ostium of the right ITV 1010. Alternatively, access to the right ITV may be achieved as shown by entering a right subclavian vein access point 1030 in a mirror image procedure of that used to obtain the left subclavian access 970. In either example, once the distal end 984 of the lead pulling tool 214 is in the ITV 1010, the lead 100 may be implanted in the right ITV accordingly.

Figure 11A:
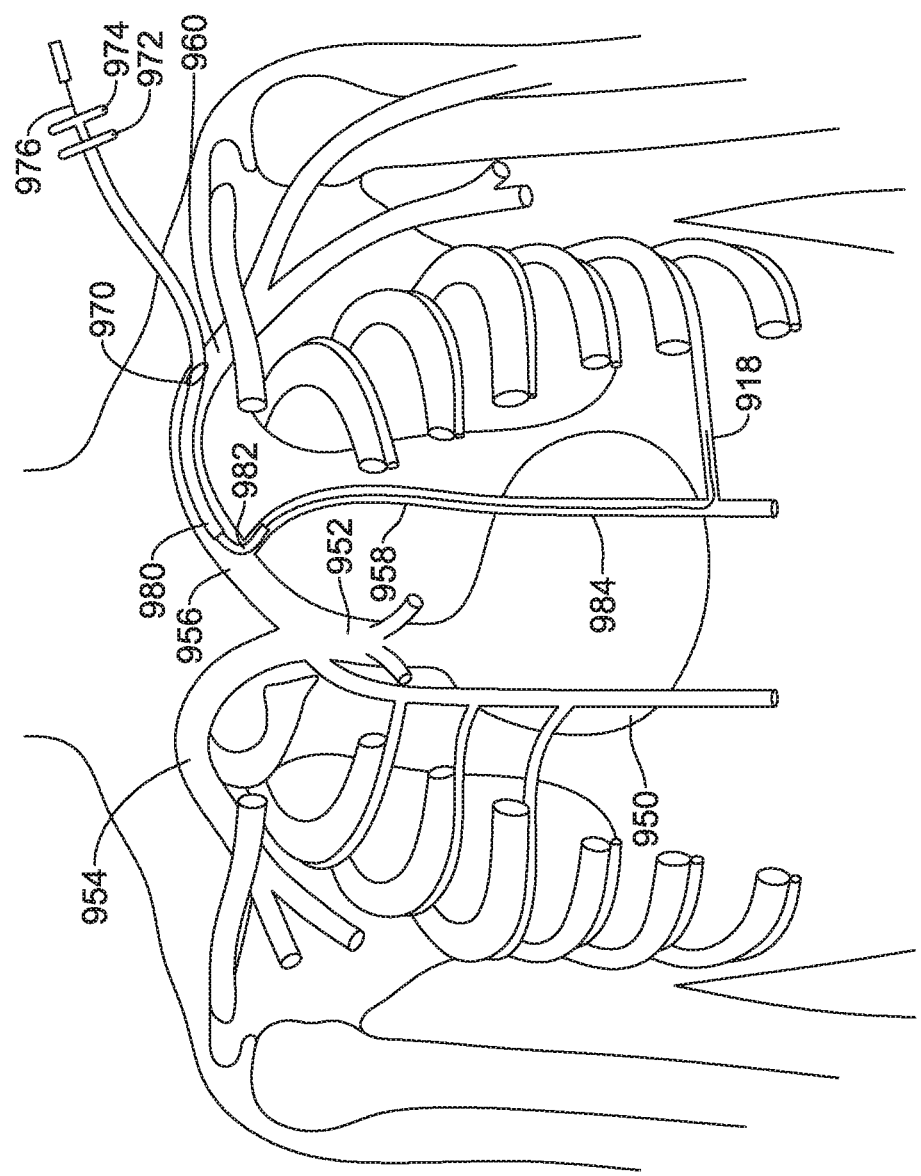
FIGS. 11A-11C show access to and implantation of the lead in the left ITV and an intercostal vein.
Figure 11B:
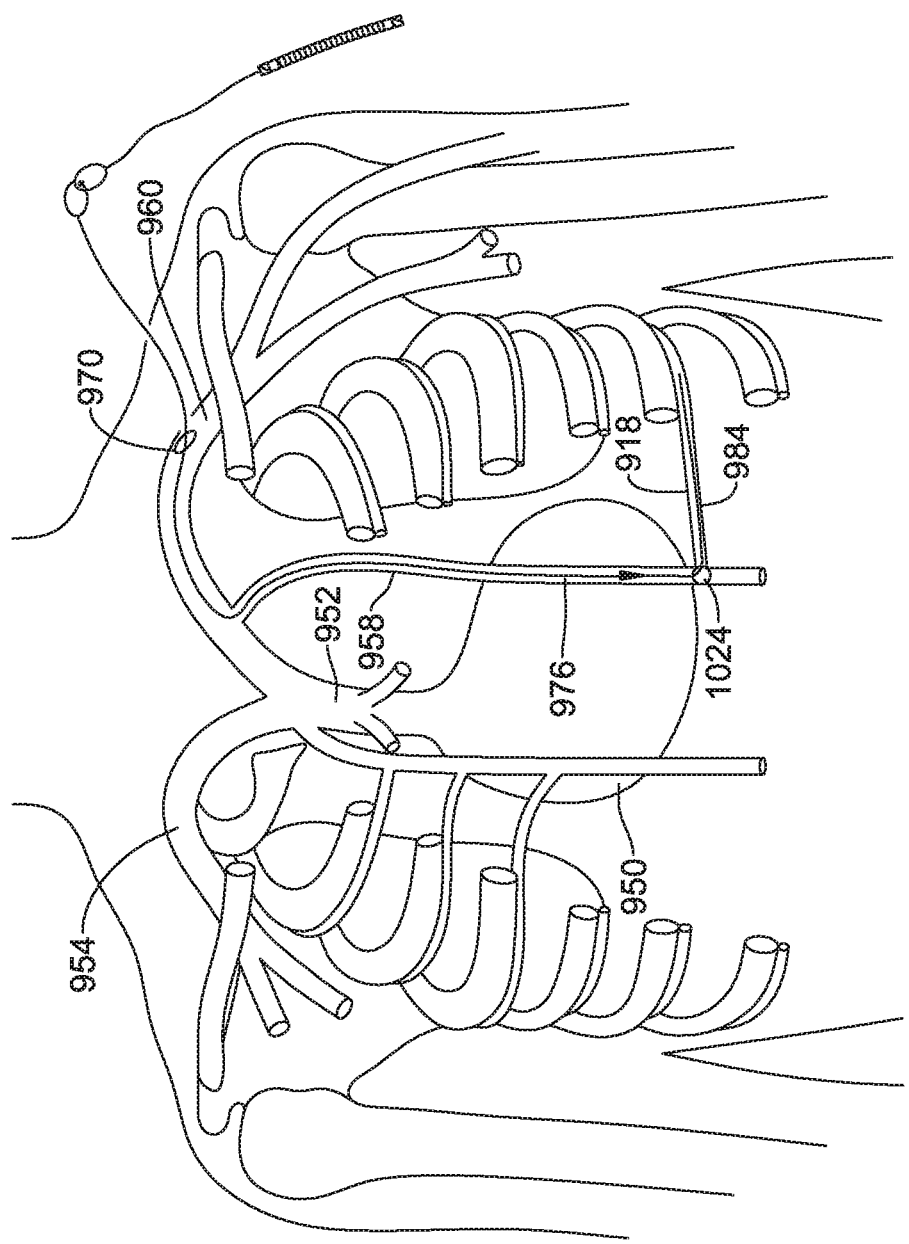
Figure 11C:
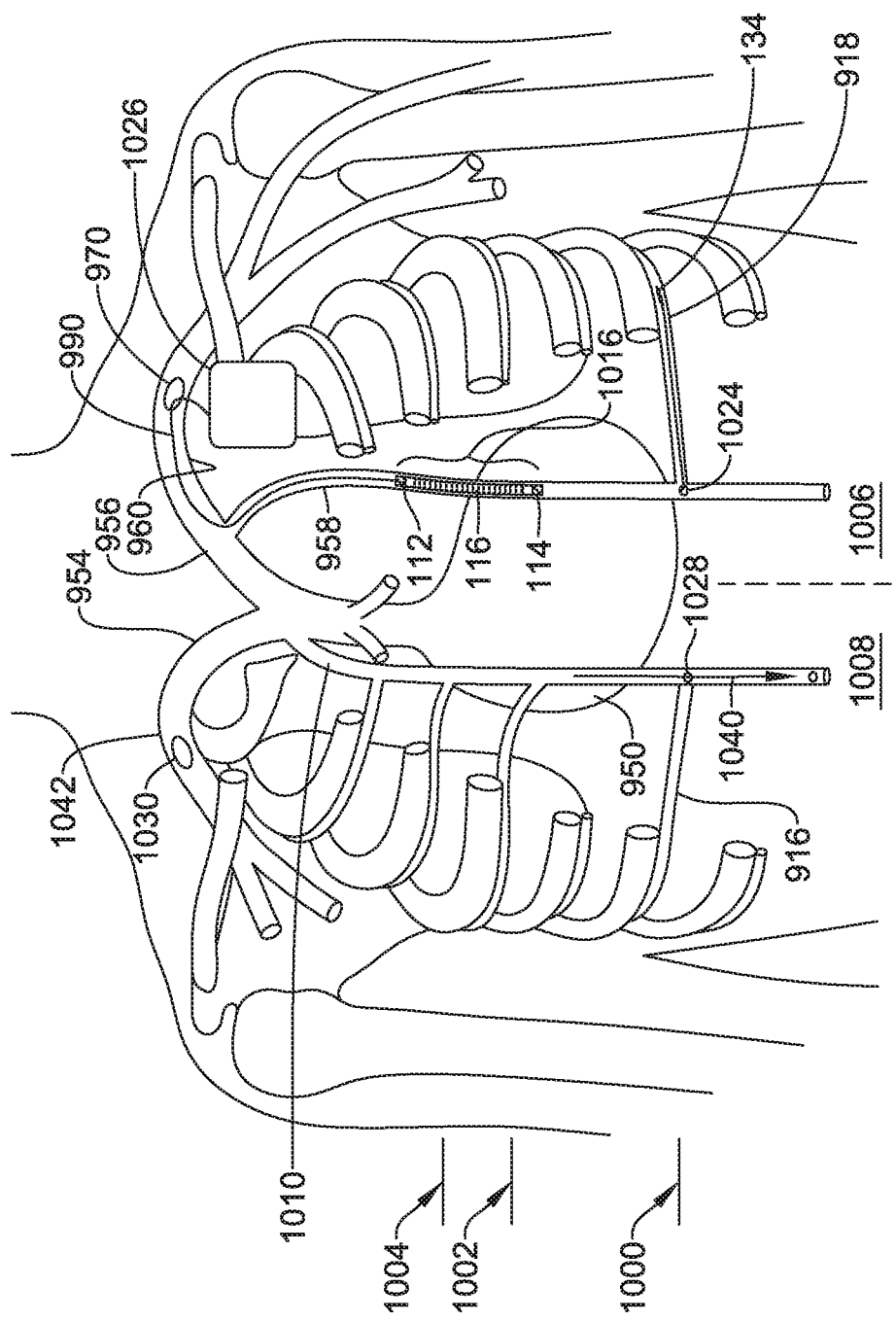

FIGS. 11A-11C show another example of access to and implantation of the lead 100 in the ITV 958. Additionally, the distal portion 106 of the lead 100 may be implanted in an intercostal vein 918. In the example shown, a $6^{th}$ intercostal vein 918 is used. A different intercostal vein may be used if desired.

Many aspects of the implantation process are similar to the implantation process described with regard to FIGS. 9A-9C. Starting with FIG. 11A, access to the subclavian vein 960 is shown at 970 using standard access techniques known in the art for implanting traditional transvenous pacemakers and defibrillators, similar to the techniques described in regard to FIG. 9A. Into the access at 970, an introducer sheath 972 is inserted and advanced to a location to place its distal tip 980 near the ostium of the left ITV 958. Contrast injection may be useful to visualize the ITV structures and the ostia of the ITVs. The guide catheter 974 and the distal end 984 of the lead pulling tool 214 may then be introduced through the introducer sheath 972. In other examples, a shorter introducer sheath may be used, with the guide catheter 974 used to traverse the distance to the relevant ostium.

In certain embodiments, the lead pulling tool 214 may be a guidewire and may be the same as used in gaining initial access 970 (if one is used to gain access 970), or may be a different a different guidewire. In an example, the lead pulling tool 214 is preloaded in the guide catheter and both are introduced at the same time until the guide catheter 974 is at a desired location relative to the ostium of the selected ITV. The distal end 984 of the lead pulling tool 214 which may be deflectable or steerable, can then be used to enter the left ITV 958 through the ostium thereof, passing down into the left ITV 958.

In some examples, the guide catheter 974 is introduced first and the lead pulling tool 214 is introduced next. For example, a steerable or curved guide catheter 974 may traverse the introducer sheath 972 to its distal end 980 and then, using steering of the guide catheter or a precurved structure of the guide catheter, would then turn as shown at 982 to enter the left ITV 958. The lead pulling tool 214 may then be introduced through the guide catheter 974, advanced into the left ITV 958, passing down into the left ITV 958, then enter the ostium from the left ITV 958 into the intercostal vein 918.

FIG. 11B shows the distal end 984 of the lead pulling tool 214 deep within the intercostal vein 918. The anchoring mechanism 404 may then be attached to the tether retention structure 400. The lead pulling tool 214 may then be located (e.g., using visualization techniques described herein) in the ITV 958. In some cases, the presence of the lead pulling tool 214 inside the intercostal vein 918 may disclose the location of the intercostal vein 918 and increase the accuracy of establishing an external access 1024 in the intercostal vein 600. Cut-down methods, known in the art, may then be used to create the external access 1024.

While maintaining the lead pulling tool's distal access to the intercostal vein 918, advancement to the ITV 958 may be achieved by pulling the distal end 984 of the lead pulling tool 214 from the external access 1024 location, as shown by arrow 1038, and drawing the lead 100 from the access point 970, into the subclavian vein 960, to the brachiocephalic vein 956, through the ostium of the ITV 958, and advancing the tether retention structure 400 of the lead 100 to the external access 1024 location to externalize the tether retention structure 400. When the tether retention structure 400 is at the external access 1024 location, the tether retention structure 400 may be detached from the anchoring mechanism 404. A dilator (not shown) and an introducer sheath (not shown) may then be used at the external access 1024 to enable the lead 100 to gain access to the intercostal vein 918. The introducer sheath may then be used to position the distal portion 106 of the lead 100 at the desired location in the intercostal vein 918 and the external access 1024 may be closed. In certain embodiments, the location of the distal portion 106 may be positioned in the intercostal vein 918 such that the tether retention structure 400 can reach a typical pulse generator location for an S-ICD.

FIG. 11C shows implantation of another implantable cardiac stimulus system. The system shown in FIG. 11C may be configured and operate similar to the system shown in FIG. 9D. In addition, the system shown in FIG. 11C may include the distal portion 106 of the lead 100 implanted in the intercostal vein 918. In certain embodiments, the distal portion 106 of the lead 100 may include a built in shocking coil. In other embodiments, as shown in FIG. 11C, the tether retention structure 400 may be attached to the rod electrode 134 (from FIG. 1E).

The illustration shown in FIG. 11C places the lead 100 on the left side 1006 of the patient. In other examples, the right side 1008 of the patient may instead or in addition be accessed, including the right ITV 1010 and a right intercostal vein 916. Implantation of the lead 100 in the right ITV 1010 and in the right intercostal vein 916 may be done using the same procedure described above for the system in FIG. 11C. However, in this embodiment, the lead pulling tool 214 is advanced from the left subclavian access 970, across to the ostium of the right ITV 1010. Alternatively, access to the right ITV may be achieved as shown by entering a right subclavian vein access point 1030 in a mirror image procedure of that used to obtain the left subclavian access 970. In either example, once the distal end 984 of the lead pulling tool 214 is in the ITV 1010, the lead 100 may be implanted in the right ITV and the right intercostal vein 916 accordingly.

Figure 11D:
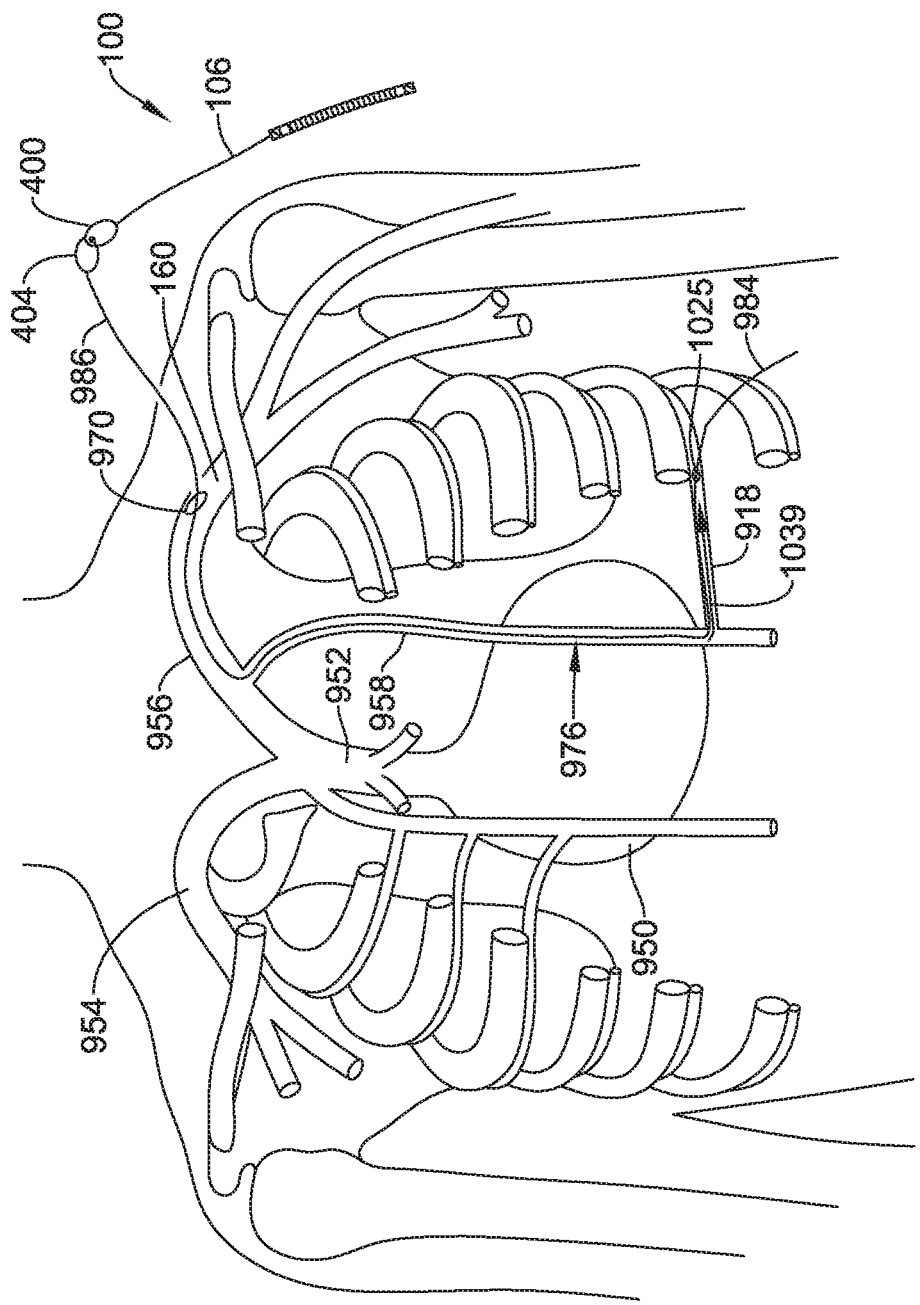
FIGS. 11D-11E show another access to and implantation of the lead in the left ITV and the intercostal vein
Figure 11E:
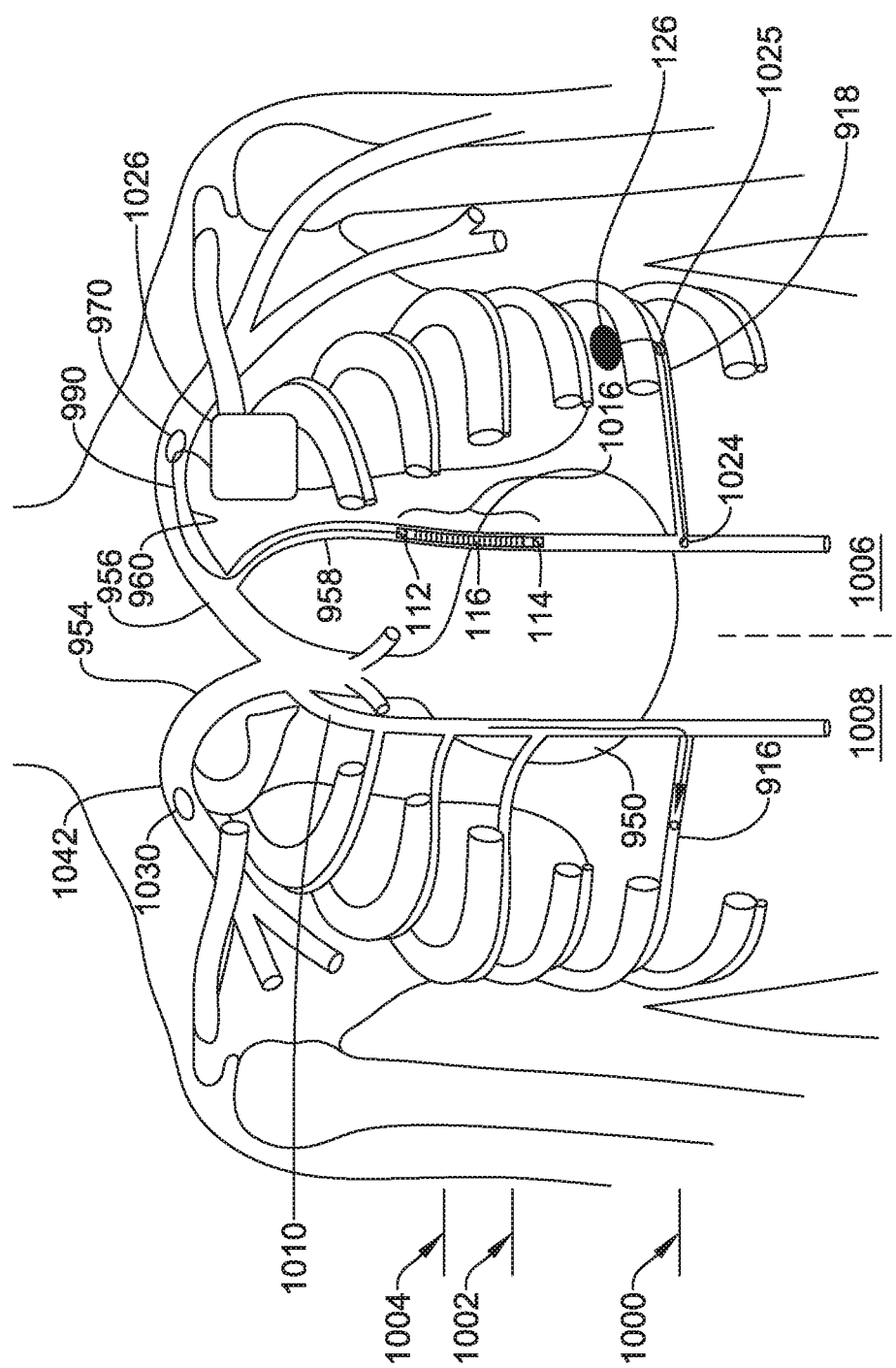

FIGS. 11D-11E show another example of access to and implantation of another implantable cardiac stimulus system. Access to the ITV 958 may be similar to the access described in regard to FIGS. 11A-11B. However, as shown in FIG. 11D, when the lead pulling tool 214 is deep within the intercostal vein 918 and the anchoring mechanism 404 is attached to tether retention structure 400, the lead pulling tool 214 may be located (e.g., using visualization techniques described herein) in the intercostal vein 918. Cut-down methods, known in the art, may then be used to create the external access 1025 to externalize the lead pulling tool 214 and expose the intercostal vein 918. Advancement to the intercostal vein 918 may be achieved by pulling the distal end 984 of the lead pulling tool 214 from the external access 1025 location, as shown by arrow 1039, and drawing the lead 100 from the access point 970, into the subclavian vein 960, to the brachiocephalic vein 956, through the ostium of the ITV 958, down the ITV 958, through the ostium of the intercostal vein 918, and advancing the tether retention structure 400 of the lead 100 to the external access 1025 location to externalize the tether retention structure 400. When the tether retention structure 400 is at the external access 1025, the tether retention structure 400 may be detached from the anchoring mechanism 404. Additionally, to implant the solid disk electrode 126, when the tether retention structure 400 is at the external access 1025 location, the connector 408 of the solid disk electrode 126 may then be attached to the tether retention structure 400 and the external access 1025 may be used to implant the solid disk electrode 126 at the left lateral position, as shown in FIG. 11E, and the external access 1025 may be closed. Rather than a solid disk electrode 126, any of the structures of FIGS. 1A-1F may be used.

The illustration shown in FIG. 11E places the lead 100 on the left side 1006 of the patient. In other examples, the right side 1008 of the patient may instead or in addition be accessed, including the right ITV 1010 and the right intercostal vein 916. Implantation of the lead 100 in the right ITV 1010 and in the right intercostal vein 916 may be done using the same procedure described above for the system in FIG. 11E. However, in this embodiment, the lead pulling tool 214 is advanced from the left subclavian access 970, across to the ostium of the right ITV 1010. Alternatively, access to the right ITV may be achieved as shown by entering a right subclavian vein access point 1030 in a mirror image procedure of that used to obtain the left subclavian access 970. In either example, once the distal end 984 of the lead pulling tool 214 is in the ITV 1010, the lead 100 may be implanted in the right ITV and the right intercostal vein accordingly.

Figure 12:
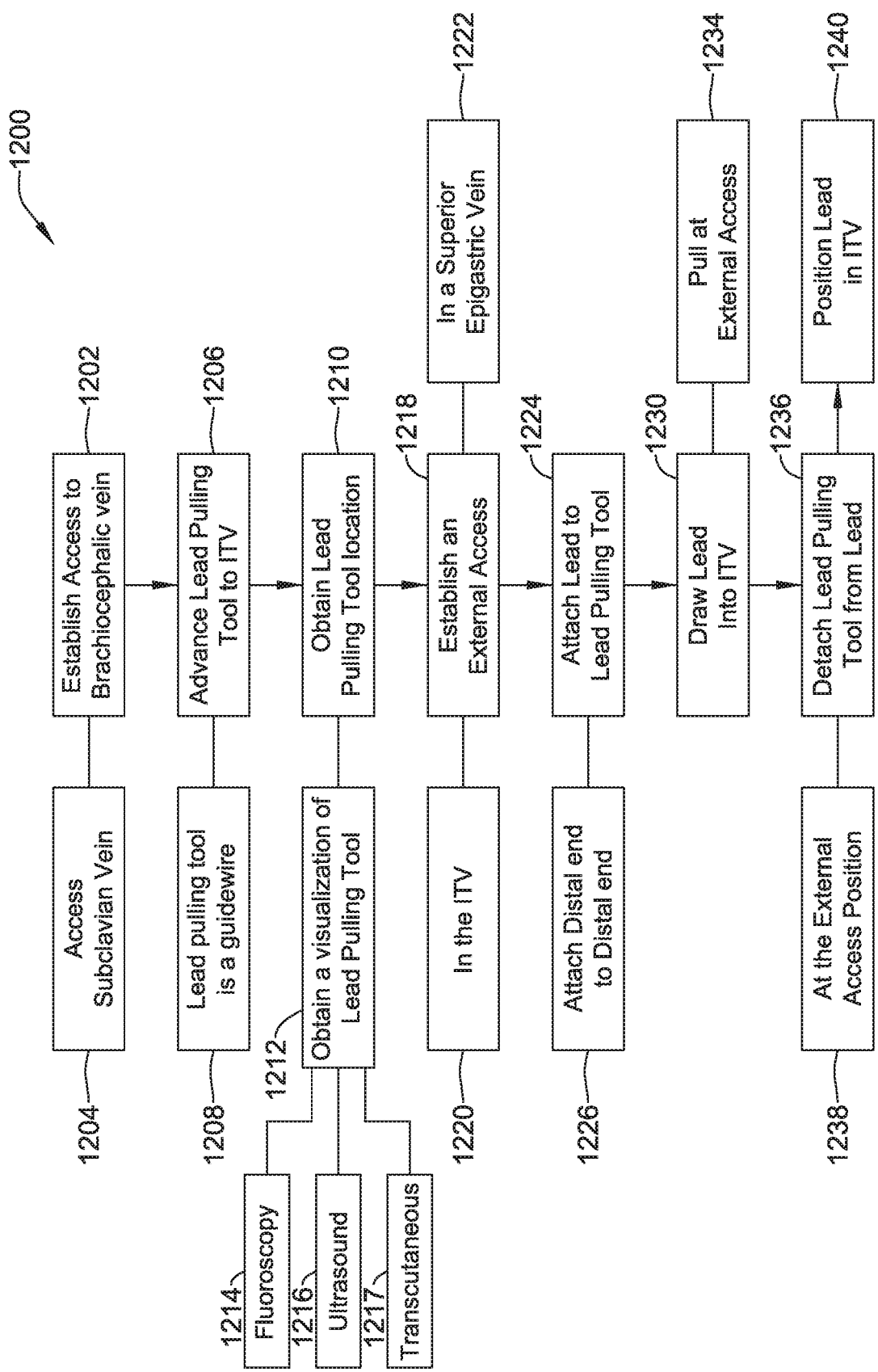
FIG. 12 is a block flow diagram for an illustrative method.

FIG. 12 is a block flow diagram for an illustrative method for implanting a lead in an ITV. As shown at 1200, the method comprises establishing access to a brachiocephalic vein 1202, advancing a lead pulling tool to an ITV 1206, obtaining the lead pulling tool location 1210, establishing an external access 1218, attaching a lead to the lead pulling tool 1224, drawing the lead into the ITV 1230, and detaching the lead pulling tool from the lead 1236.

For example, establishing access to the brachiocephalic vein 1202 may include accessing a subclavian vein 1204 and advancing into the brachiocephalic vein. Access to the subclavian vein may be done using standard access techniques known in the art for implanting traditional transvenous pacemakers and defibrillators. For example, the Seldinger technique may be used or other venipuncture or cutdown techniques. Other vessels may be accessed instead of the subclavian vein using similar techniques including, for example, the jugular, cephalic, or axillary veins.

In an example, advancing the lead pulling tool to the ITV 1206 may include passing through an ostium of the ITV in the brachiocephalic vein. In some examples, the lead pulling tool may be a guidewire 1208 and may be the same as used in establishing access to the brachiocephalic vein 1202. The lead pulling tool may be instead a stylet, a hypotube, or a catheter having sufficient column strength to allow pushing through blood vessels to desired position, and further with sufficient strength to allow pulling of a lead. In another example, the lead pulling tool may be a combination of a guide catheter and guidewire and are introduced at the access location and the guide catheter is advanced to a desired location relative to the ostium of the ITV. The lead pulling tool, which may be deflectable or steerable, can then be used to enter the ITV through the ostium thereof, passing down into the ITV.

In an example, obtaining the lead pulling tool location 1210 may include obtaining a visualization of the lead pulling tool 1212. In some examples, the lead pulling tool may be a radiopaque guidewire. In other cases, a radiopaque material may be placed over the lead pulling tool. When the lead pulling tool is inside the ITV the lead pulling tool may then be visualized, for example, using fluoroscopy 1214, an ultrasound 1216, or an LED may be positioned at or near the distal tip of the lead pulling tool to allow transcutaneous visualization 1217. The lead pulling tool may then be observed and adjusted inside the ITV to a desired location. In some examples, a physician may use the fluoroscope image to identify the lead pulling tool and place forceps in the view range of the fluoroscope to get a surface position of the lead pulling tool. In some examples, the surface position of the lead pulling tool may be obtained using fluoroscope imaging to identify the lead pulling tool and an x-ray may be used to identify the xiphoid. In some cases, instead of an x-ray, ultrasound imaging may be used to identify the xiphoid. In some cases, fluoroscopy may not be used and ultrasound imaging may be used to identify the lead pulling tool and the physician may use an ultrasound needle in the view range of the ultrasound to establish the position of the lead pulling tool. In still further embodiments, a special lead pulling tool may be used that discloses its position in some shape or form in the ITV.

In an example, establishing an external access 1218 may include using one of the visualization techniques described above or another conventional locating or visualization technique known by those skilled in the art to establish the external access position in the ITV 1220 or in a superior epigastric vein 1222.

In an example, attaching the lead to the lead pulling tool 1224 may include attaching an attachment feature of the lead to a proximal tip portion of the lead pulling tool 1226. In some examples, the proximal end of the lead pulling tool may include the proximal tip portion and a distal portion of the lead may include the compatible attachment feature to the proximal tip portion.

In an example, drawing the lead into the ITV 1230 may include pulling the distal end of the lead pulling tool 1234. In some examples, the distal end of the lead pulling tool may be located near the external access position and advancement to the ITV may be achieved by pulling the distal end of the lead pulling tool from the external access location, and drawing the lead inferiorly from the superior access point, into the subclavian vein, to the brachiocephalic vein, through the ostium of the ITV, and advancing the attachment feature of the lead to the external access position.

In an example, detaching the lead pulling tool from the lead 1236 may include detaching the proximal tip portion of the lead pulling tool from the attachment feature of the lead at the external access position.

In an example, the lead may be placed at the desired position within the ITV 1240 using an introducer sheath.

Figure 13:
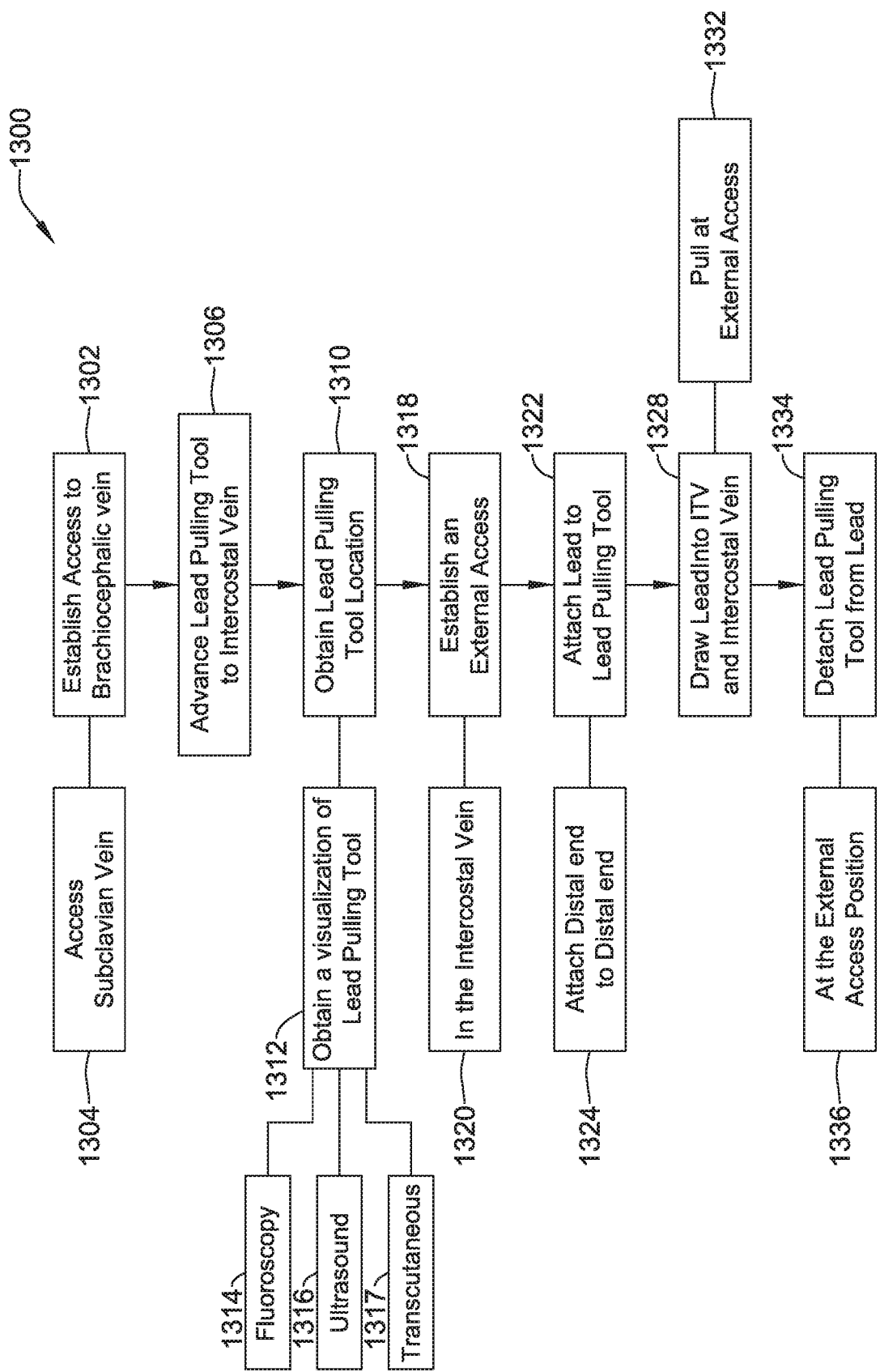
FIG. 13 is a block flow diagram for another illustrative method.

FIG. 13 is a block flow diagram for an illustrative method for implanting a lead in an ITV and an intercostal vein. As shown at 1300, the method comprises establishing access to a brachiocephalic vein 1302, advancing a lead pulling tool 1306, obtaining the lead pulling tool location 1310, establishing an external access 1318, attaching a lead to the lead pulling tool 1322, drawing the lead into the ITV and intercostal vein 1328, and detaching the lead pulling tool from the lead 1334.

For example, establishing access to the brachiocephalic vein 1302 may be done similar to the examples discussed in regard to step 1202, of flow diagram 1200. In an example, advancing the lead pulling tool to an intercostal vein 1306 may be done similar to advancing the lead pulling tool to an ITV as discussed in regard to step 1206, of flow diagram 1200. In addition, further advancement of the lead pulling tool from the ITV to the intercostal vein may be achieved by passing down into the ITV, and entering an ostium from the ITV into the intercostal vein. In an example, obtaining the lead pulling tool location 1310 may be done similar to the examples discussed in regard to step 1210, of flow diagram 1200. In an example, establishing an external access position 1318 maybe done similar to the examples discussed in regard to step 1218, of flow diagram 1200. However, in this case, the visualization techniques or other conventional locating or visualization techniques known by those skilled in the art may be used to establish the external access position in the intercostal vein 1320. In an example, attaching the lead to the lead pulling tool 1322 may be done similar to the examples discussed in regard to step 1224, of flow diagram 1200.

In an example, drawing the lead into the ITV and the intercostal vein 1328 may include pulling the distal end of the lead pulling tool 1232. In some examples, the distal end of the lead pulling tool may be located near the external access position and advancement to the ITV and the intercostal vein 1328 may be achieved by pulling the distal end of the lead pulling tool from the external access location, and drawing the lead from the access point, into the subclavian vein, to the brachiocephalic vein, through the ostium of the ITV, down the ITV, through the ostium of the intercostal vein, and advancing the attachment feature of the lead to the external access position.

In an example, detaching the lead pulling tool from the lead 1334 may be done similar to the examples discussed in regard to step 1236, of flow diagram 1200.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L that is generally larger than a width W. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of implanting a lead for use in a cardiac stimulus system in a patient, the lead having a proximal end and a distal end, the distal end comprising an attachment feature, the method using a lead pulling tool having a distal end adapted for advancement into the vasculature of the patient and a proximal end having a coupler for mechanical coupling to the attachment feature of the lead, the method comprising:
    establishing venous access into the patient;
    advancing the distal end of the lead pulling tool into a brachiocephalic vein;
    advancing the distal end of the lead pulling tool from the brachiocephalic vein into an internal thoracic vein (ITV);
    obtaining a location of the lead pulling tool in the venous vasculature;
    establishing an external access to the venous vasculature in order to access the distal end of the lead pulling tool;
    securing the lead attachment feature to the lead pulling tool coupler; and
    drawing the lead at least into the ITV by pulling the lead pulling tool out of the patient using the external access.

2. The method of claim 1, further comprising detaching the lead attachment feature from the lead pulling tool coupler, securing an electrode to the lead attachment feature, and implanting the electrode at a subcutaneous location.

3. The method of claim 1 further comprising advancing the lead pulling tool into an intercostal vein, wherein the external access is made by accessing the intercostal vein, such that the lead is implanted with a portion thereof extending within the intercostal vein.

4. The method of claim 1 further comprising advancing the lead subcutaneously from the location of the external access to a desired subcutaneous location, detaching the lead attachment feature from the lead pulling tool coupler, and attaching an electrode to the lead attachment feature.

5. The method of claim 4 wherein the electrode is a mesh patch electrode, and the method further comprises implanting the mesh patch electrode at the desired subcutaneous location.

6. The method of claim 4 wherein the electrode is a solid disk electrode, and the method further comprises implanting the solid disk electrode at the desired subcutaneous location.

7. The method of claim 4 wherein the electrode is a coil electrode, and the method further comprises implanting the coil electrode at the desired subcutaneous location.

8. The method of claim 4 wherein the electrode is a rod electrode, and the method further comprises implanting the rod electrode at the desired subcutaneous location.

9. The method of claim 4 wherein the electrode is a jointed disk array electrode, and the method further comprises implanting the jointed disk array electrode at the desired subcutaneous location.

10. The method of claim 1 wherein the attachment feature is a tether retention structure having a hole for receiving a tether, hook or fastener.

* * * * *